US008426214B2

(12) United States Patent
Stayton et al.

(10) Patent No.: US 8,426,214 B2
(45) Date of Patent: Apr. 23, 2013

(54) SYSTEM AND METHOD FOR MAGNETICALLY CONCENTRATING AND DETECTING BIOMARKERS

(75) Inventors: Patrick S. Stayton, Seattle, WA (US); Michael Nash, Seattle, WA (US); Jriuan Lai, Seattle, WA (US)

(73) Assignee: University of Washington, Seattle, WA (US)

( * ) Notice: Subject to any disclaimer, the term of this patent is extended or adjusted under 35 U.S.C. 154(b) by 406 days.

(21) Appl. No.: 12/815,217

(22) Filed: Jun. 14, 2010

(65) Prior Publication Data

US 2011/0003392 A1 Jan. 6, 2011

Related U.S. Application Data

(60) Provisional application No. 61/259,545, filed on Nov. 9, 2009, provisional application No. 61/186,780, filed on Jun. 12, 2009.

(51) Int. Cl.
*C12M 1/00* (2006.01)
*G01N 31/00* (2006.01)
*G01N 31/22* (2006.01)
*G01N 9/00* (2006.01)

(52) U.S. Cl.
USPC ............. 436/149; 436/86; 436/169; 436/148; 436/150; 436/94; 436/93; 436/91; 435/173.1; 435/173.9

(58) Field of Classification Search ............. 436/86, 436/169, 150, 149, 94, 93, 91; 435/173.1, 435/173.9; 422/65, 64, 50
See application file for complete search history.

(56) References Cited

U.S. PATENT DOCUMENTS

| 4,332,690 A | 6/1982 | Kimura |
| 4,657,543 A | 4/1987 | Langer |
| 4,780,409 A | 10/1988 | Monji |
| 5,135,876 A | 8/1992 | Andrade |
| 5,356,713 A | 10/1994 | Charmot |
| 5,362,308 A | 11/1994 | Chien |
| 5,378,608 A | 1/1995 | Marui |
| 5,451,411 A | 9/1995 | Gombotz |

(Continued)

FOREIGN PATENT DOCUMENTS

| DE | 697 06 501 T2 | 5/2002 |
| DE | 102 24 352 A1 | 12/2003 |

(Continued)

OTHER PUBLICATIONS

Akiyoshi, K., et al., "Controlled Association of Amphiphilic Polymers in Water: Thermosensitive Nanoparticles Formed by Self-Assembly of Hydrophobically Modified Pullulans and Poly(N-isopropylacrylamides)," Macromolecules 33(9):3244-3249, May 2000.

(Continued)

*Primary Examiner* — Christine T Mui
(74) *Attorney, Agent, or Firm* — Christensen O'Connor Johnson Kindness PLLC

(57) ABSTRACT

System and method for capturing, concentrating, and detecting a diagnostic target in a liquid, comprising applying a magnetic field to a mixture comprising a co-aggregate in the liquid to provide a collected co-aggregate in the liquid, wherein the co-aggregate comprises a magnetic particle having a stimuli-responsive polymer attached thereto and a non-magnetic particle having a stimuli-responsive polymer and a diagnostic target attached thereto.

11 Claims, 22 Drawing Sheets
(8 of 22 Drawing Sheet(s) Filed in Color)

U.S. PATENT DOCUMENTS

| | | | |
|---|---|---|---|
| 5,466,348 A | 11/1995 | Holm-Kennedy |
| 5,501,584 A | 3/1996 | Yamamoto |
| 5,521,291 A | 5/1996 | Curiel |
| 5,547,932 A | 8/1996 | Curiel |
| 5,569,364 A | 10/1996 | Hooper |
| 5,599,908 A | 2/1997 | Raso |
| 5,603,931 A | 2/1997 | Raso |
| 5,609,590 A | 3/1997 | Herbig |
| 5,656,609 A | 8/1997 | Wu |
| 5,753,263 A | 5/1998 | Lishko |
| 5,770,627 A | 6/1998 | Inoue |
| 5,807,306 A | 9/1998 | Shapland |
| 5,827,743 A | 10/1998 | Tanzawa |
| 5,876,989 A | 3/1999 | Berg |
| 5,939,453 A | 8/1999 | Heller |
| 5,997,961 A | 12/1999 | Feng |
| 5,998,588 A | 12/1999 | Hoffman |
| 6,133,047 A | 10/2000 | Elaissari |
| 6,165,509 A | 12/2000 | Hoffman |
| 6,210,717 B1 | 4/2001 | Choi |
| 6,355,163 B2 | 3/2002 | Hindsgaul |
| 6,426,086 B1 | 7/2002 | Papahadjopoulos |
| 6,447,764 B1 | 9/2002 | Bayer |
| 6,486,213 B1 | 11/2002 | Chen |
| 6,521,341 B1 | 2/2003 | Elaissari |
| 6,641,735 B2 | 11/2003 | Yoshizako |
| 6,740,409 B1 | 5/2004 | Granick |
| 6,835,393 B2 | 12/2004 | Hoffman |
| 7,060,804 B2 | 6/2006 | Elaissari |
| 7,195,925 B2 | 3/2007 | Ohnishi |
| 7,393,698 B2 | 7/2008 | Furukawa |
| 7,625,764 B2 | 12/2009 | Stayton |
| 7,695,905 B2 | 4/2010 | Furukawa |
| 7,718,193 B2 | 5/2010 | Stayton |
| 7,732,550 B2 | 6/2010 | Ohnishi |
| 7,976,728 B2 | 7/2011 | Eguchi |
| 7,981,688 B2 | 7/2011 | Stayton |
| 8,105,493 B2 | 1/2012 | Takahashi |
| 2001/0027072 A1 | 10/2001 | Mumick |
| 2003/0165962 A1 | 9/2003 | Furukawa |
| 2003/0175691 A1 | 9/2003 | Elaissari |
| 2003/0175826 A1 | 9/2003 | Furukawa |
| 2003/0218130 A1 | 11/2003 | Boschetti |
| 2004/0077024 A1 | 4/2004 | Holmberg |
| 2004/0239738 A1 | 12/2004 | Watanabe |
| 2005/0124728 A1 | 6/2005 | Komatsu |
| 2005/0130167 A1 | 6/2005 | Bao |
| 2005/0137334 A1 | 6/2005 | Mondain-Monval |
| 2005/0158782 A1 | 7/2005 | Furukawa |
| 2005/0175702 A1 | 8/2005 | Müller-Schulte |
| 2007/0218567 A1 | 9/2007 | Tanaka |
| 2008/0199884 A1 | 8/2008 | Ohnishi |
| 2008/0220531 A1 | 9/2008 | Stayton |
| 2008/0293118 A1 | 11/2008 | Furukawa |
| 2009/0001025 A1 | 1/2009 | Takahashi |
| 2009/0001321 A1 | 1/2009 | Eguchi |
| 2010/0062433 A1 | 3/2010 | Nagaoka |
| 2010/0168044 A1 | 7/2010 | Misra |
| 2010/0215749 A1 | 8/2010 | Stayton |
| 2010/0330688 A1 | 12/2010 | Sawai |
| 2011/0014713 A1 | 1/2011 | Sawai |
| 2011/0097416 A1 | 4/2011 | Nguyen |
| 2011/0117668 A1 | 5/2011 | Stayton |
| 2011/0120919 A1 | 5/2011 | Domke |
| 2011/0155947 A1 | 6/2011 | Eguchi |
| 2011/0233453 A1 | 9/2011 | Eguchi |
| 2011/0266492 A1 | 11/2011 | Stayton |

FOREIGN PATENT DOCUMENTS

| | | |
|---|---|---|
| DE | 698 39 323 T2 | 4/2009 |
| EP | 0 693 508 A1 | 8/1995 |
| EP | 1 281 436 A1 | 8/1995 |
| EP | 1 312 671 A1 | 5/2003 |
| EP | 1 316 599 A1 | 6/2003 |
| EP | 1 396 508 A1 | 10/2004 |
| EP | 1 803 467 A1 | 7/2007 |
| EP | 2 009 044 A1 | 12/2008 |
| EP | 2 009 442 A2 | 12/2008 |
| EP | 2 037 272 A1 | 3/2009 |
| EP | 1 509 246 B1 | 5/2009 |
| EP | 2 237 036 A1 | 10/2010 |
| EP | 2 246 701 A1 | 11/2010 |
| EP | 2 313 200 A1 | 4/2011 |
| EP | 2 320 437 A1 | 5/2011 |
| GB | 2 439 846 B | 10/2009 |
| GB | 2 435 647 B | 3/2010 |
| GB | 2 431 472 B | 4/2011 |
| JP | 2002-223793 A | 8/2002 |
| JP | 2004-201648 A | 7/2004 |
| JP | 2005-060244 A | 3/2005 |
| JP | 2005-082538 A | 3/2005 |
| JP | 2005-537342 A | 12/2005 |
| JP | 2006-194635 A | 7/2006 |
| JP | 2006-208368 A | 8/2006 |
| JP | 2006-242597 A | 9/2006 |
| JP | 2006-327962 A | 12/2006 |
| JP | 2007-056094 A | 3/2007 |
| JP | 2007-248349 A | 9/2007 |
| JP | 2007-256024 A | 10/2007 |
| JP | 2007-262388 A | 10/2007 |
| JP | 2008-232716 A | 10/2008 |
| JP | 2009-013207 A | 1/2009 |
| JP | 2009-028711 A | 2/2009 |
| JP | 2009-162532 A | 7/2009 |
| JP | 2009-162534 A | 7/2009 |
| JP | 2009-171853 A | 8/2009 |
| JP | 2009-189306 A | 8/2009 |
| JP | 2009-281728 A | 12/2009 |
| JP | 2010-032360 A | 2/2010 |
| JP | 2010-062444 A | 3/2010 |
| JP | 2010-066200 A | 3/2010 |
| JP | 2010-151528 A | 7/2010 |
| JP | 2010-235441 A | 10/2010 |
| WO | 00/43355 A1 | 7/2000 |
| WO | 01/51092 A2 | 7/2001 |
| WO | 02/16528 A1 | 2/2002 |
| WO | 02/16571 A1 | 2/2002 |
| WO | 03/055590 A2 | 7/2003 |
| WO | 2005/021612 A1 | 3/2005 |
| WO | 2006/022340 A1 | 3/2006 |
| WO | 2008/111687 A1 | 9/2008 |
| WO | 2009/084595 A1 | 7/2009 |
| WO | 2009/126441 A1 | 10/2009 |
| WO | 2009/140421 A2 | 11/2009 |
| WO | 2009/140429 A2 | 11/2009 |
| WO | 2009/140432 A1 | 11/2009 |
| WO | 2010/007157 A1 | 1/2010 |
| WO | 2010/021770 A1 | 2/2010 |
| WO | 2010/053597 A1 | 5/2010 |

OTHER PUBLICATIONS

Buchholz, B.A., et al., "Microchannel DNA Sequencing Matrices With Switchable Viscosities," Electrophoresis 23(10):1398-1409, May 2002.

Guo, J., et al., "Poly(N-isopropylacrylamide)-Coated Luminescent/Magnetic Silica Microspheres: Preparation, Characterization, and Biomedical Applications," Chemistry of Materials 18(23):5554-5562, Nov. 2006.

Hoffman, A.S., et al., "Really Smart Bioconjugates of Smart Polymers and Receptor Proteins," Journal of Biomedical Materials Research 52(4):577-586, Dec. 2000.

Irie, M., "Stimuli-Responsive Poly(N-isopropylacrylamide). Photo- and Chemical-Induced Phase Transitions," in K. Dušek (ed.), vol. 110, "Responsive Gels: Volume Transitions II," "Advances in Polymer Science," Springer-Verlag, Berlin, 1993, pp. 49-65.

Kanazawa, H., and Y. Matsushima, "Temperature-Responsive Chromatography," Trends in Analytical Chemistry 17(7):435-440, Aug. 1998.

Kondo, A., et al., "Development and Application of Thermo-Sensitive Magnetic Immunomicrospheres for Antibody Purification," Applied Microbiology and Biotechnology 41(1):99-105, Mar. 1994.

Kulkarni, S., et al., "Reversible Meso-Scale Smart Polymer—Protein Particles of Controlled Sizes," Bioconjugate Chemistry 15(4):747-753, Jul. 2004.

Li, M., et al., "Organization of Inorganic Nanoparticles Using Biotin-Streptavidin Connectors," Chemistry of Materials 11(1):23-26, Jan. 1999.

Malmstadt, N., et al., "A Smart Microfluidic Affinity Chromatography Matrix Composed of Poly(N-isopropylacrylamide)-Coated Beads," Analytical Chemistry 75(13):2943-949, Jul. 2003.

Malmstadt, N., et al., "'Smart' Mobile Affinity Matrix for Microfluidic Immunoassays," Lab on a Chip 4(4):412-415, Aug. 2004.

Matsubara, C., et al., "Determination of Trace Amounts of Phosphate in Water After Preconcentration Using a Thermally Reversible Polymer," Analyst 118(5):553-556, May 1993.

Miura, M., et al., "Application of LCST Polymer-Cell Receptor Conjugates for Cell Culture on Hydrophobic Surfaces," 17th Annual Meeting of the Society for Biomaterials, Scottsdale, Ariz., May 1-5, 1991, p. 130.

Monji, N., and A.S. Hoffman, "A Novel Immunoassay System and Bioseparation Process Based on Thermal Phase Separating Polymers," Applied Biochemistry and Biotechnology 14(2):107-120, Mar. 1987.

Monji, N., et al., "Application of a Thermally-Reversible Polymer—Antibody Conjugate in a Novel Membrane-Based Immunoassay," Biochemical and Biophysical Research Communications 172(2):652-660, Oct. 1990.

Tang, Z., et al., "Single Nucleotide Polymorphisms (SNPs) Assay Using Reversible Association and Dispersion of DNA-Linked Colloidal Nanoparticles," Nucleic Acids Research: Supplement No. 1, Nov. 2001, pp. 165-166.

Yoshizako, K., and Y. Akiyama, "Regulation of Protein Binding Toward a Ligand on Chromatographic Matrixes by Masking and Forced-Releasing Effects Using Thermoresponsive Polymer," Analytical Chemistry 74(16):4160-4166, Aug. 2002.

International Search Report and Written Opinion mailed Feb. 22, 2012, issued in corresponding International Application No. PCT/US2011/040385, filed Jun. 14, 2011,10 pages.

Nash, M.A., et al., "Mixed Stimuli-Responsive Magnetic and Gold Nanoparticle System for Rapid Purification, Enrichment, and Detection of Biomarkers," Bioconjugate Chemistry 21(12):2197-2204, Dec. 2010.

Nash, M.A., et al., "'Smart' Diblock Copolymers as Templates for Magnetic-Core Gold-Shell Nanoparticle Synthesis," Nano Letters 10(1):85-91, Jan. 2010.

Frey, N.A., et al., "Magnetic Nanoparticles: Synthesis, Functionalization, and Applications in Bioimaging and Magnetic Energy Storage," Chemical Society Reviews 38(9):2532-2542, Sep. 2009.

Kondo, A., and H. Fukuda, "Preparation of Thermo-Sensitive Magnetic Hydrogel Microspheres and Application to Enzyme Immobilization," Journal of Fermentation and Bioengineering 84(4):337-341, Jan. 1997.

Abu-Lail, N.I., et al., "Micro-Cantilevers With End-Grafted Stimulus-Responsive Polymer Brushes for Actuation and Sensing," Sensors and Actuators, B: Chemical 114(1):371-378, Mar. 2006.

Garcia, I., et al., "Generation of Core/Shell Iron Oxide Magnetic Nanoparticles With Polystyrene Brushes by Atom Transfer Radical Polymerization," Journal of Polymer Science: Part A: Polymer Chemistry 45(20):4744-4750, Oct. 2007.

Matsuno, R., et al., "Polystyrene- and Poly(3-vinylpyridine)-Grafted Magnetite Nanoparticles Prepared Through Surface-Initiated Nitroxide-Mediated Radical Polymerization," Macromolecules 37(6):2203-2209, Mar. 2004.

Medeiros, S.F., et al., "Stimuli-Responsive Magnetic Particles for Biomedical Applications," International Journal of Pharmaceutics 403(1-2)139-161, Jan. 2011.

Thorek, D.L.J., et al., "Superparamagnetic Iron Oxide Nanoparticle Probes for Molecular Imaging," Annals of Biomedical Engineering 34(1):23-38, Jan. 2006.

Uhlmann, P., et al., "Surface Functionalization by Smart Coatings: Stimuli-Responsive Binary Polymer Brushes," Progress in Organic Coatings 55(2):168-174, Feb. 2006.

Wu, W., et al., "Magnetic Iron Oxide Nanoparticles: Synthesis and Surface Functionalization Strategies," Nanoscale Research Letters 3(11):397-415, Oct. 2008.

Zhang, S., et al., "Preparation and Characterization of Thermosensitive PNIPAA-Coated Iron Oxide Nanoparticles," Nanotechnology 19(32):325608, Aug. 2008, 4 pages.

Golden, A.L, et al., "Simple Fluidic System for Purifying and Concentrating Diagnostic Biomarkers Using Stimuli Responsive Antibody Conjugates and Membranes," Bioconjugate Chemistry 21(10):1820-1826, Oct. 2010.

Hoffman, J.M., et al., "A Helical Flow, Circular Microreactor for Separating and Enriching 'Smart' Polymer—Antibody Capture Reagents," Lab on a Chip 10(22):3130-3138, Nov. 2010.

International Search Report and Written Opinion,mailed Sep. 15, 2011, issued in corresponding International Application No. PCT/US2011/035256, filed May 4, 2011, 12 pages.

Lai, J.J., et al., "Dual Magnetic-/Temperature-Responsive Nanoparticles for Microfluidic Separations and Assays," Langmuir 23(13):7385-7391, Jun. 2007.

SYSTEM AND METHOD FOR MAGNETICALLY CONCENTRATING AND DETECTING BIOMARKERS

CROSS-REFERENCES TO RELATED APPLICATIONS

This application claims the benefit of U.S. Provisional Application No. 61/186,780, filed Jun. 12, 2009, and U.S. Provisional Application No. 61/259,545, filed Nov. 9, 2009, each incorporated herein by reference in its entirety.

STATEMENT OF GOVERNMENT LICENSE RIGHTS

This invention was made with Government support under Grant No. EB000252 awarded by National Institutes of Health. The Government has certain rights in the invention.

BACKGROUND OF THE INVENTION

Diagnostic testing is expanding from centralized hospital labs to more distributed settings in both the developed and developing worlds. A current dominant point-of-care diagnostic test format is the lateral flow immunoassay (LFIA), which relies on capillary wicking of fluids through porous nitrocellulose strips. Such tests typically rely on the specific binding between gold-labeled biomarkers with capture antibodies immobilized at the test line of the solid phase. Current devices possess many desirable features, such as being rapid, inexpensive, portable, and easy to use. However, these devices suffer from a limitation in sensitivity related to the small sample volume that limits the biomarker repertoire to those at relatively higher blood and plasma concentrations. These limitations have created a need for rapid and simple sample processing strategies for purifying and enriching biomarkers in a form that could then be applied directly to the existing lateral flow tests or other types of newly developed rapid tests.

The lateral flow or "dipstick" immunochromatographic assay represents a current dominant point-of-care technology capable of rapidly detecting protein biomarkers in bodily fluids (e.g., blood, urine) that is compatible with the constraints of low resource settings, such as lack of electricity and optical instrumentation. These advantages have led to widespread acceptance and consolidation within the marketplace of "dipstick" type products that are profitably manufactured and sold to consumers as rapid diagnostic tests.

However, as noted above, the range of biomarkers that are detectable by immunochromatography is ultimately limited to proteins of relatively high abundance in the plasma in part because of the inability of an immunochromatographic flow strip to process larger volumes of biological sample so as to accumulate sufficient quantities of dilute labeled biomarkers to generate a detectable signal. This deficiency has created a need for simple yet robust biomarker purification/enrichment strategies that can improve test sensitivity while leveraging the success and widespread acceptance of lateral flow rapid diagnostic tests.

Despite the advances in the development of diagnostic testing methods and devices for expanding from centralized hospital labs to more distributed settings, a need exists for improved diagnostic testing methods and devices that overcome the disadvantages of those presently used. The present invention seeks to fulfill this need and provides further related advantages.

SUMMARY OF THE INVENTION

The present invention provides systems and methods for capturing, concentrating, and detecting biomarkers.

In one embodiment, the invention provides a method for concentrating a non-magnetic particle in a liquid. In the method, a magnetic field is applied to a mixture comprising a co-aggregate in a liquid to provide a collected co-aggregate, wherein the co-aggregate comprises:

(a) a magnetic particle having a stimuli-responsive polymer attached thereto; and (b) a non-magnetic particle having a stimuli-responsive polymer attached thereto.

In one embodiment, the non-magnetic particle further comprises a diagnostic target attached thereto.

In another embodiment, the invention provides a method for capturing a diagnostic target in a liquid medium. The method includes the steps of:

(a) contacting a liquid medium to be tested for the presence of a diagnostic target with a plurality of stimuli-responsive particles, wherein the plurality of stimuli-responsive particles comprises
  (i) a plurality of magnetic particles, each having a stimuli-responsive polymer attached thereto, and
  (ii) a plurality of non-magnetic particles, each having a stimuli-responsive polymer and a capture moiety attached thereto, wherein the capture moiety has an affinity to the diagnostic target,
wherein the plurality of stimuli-responsive particles is contacted with the liquid medium for a pre-determined period of time sufficient to effect binding of the diagnostic target, if present, to a portion of the plurality of non-magnetic particles;

(b) applying an external stimulus to provide a co-aggregate in the liquid medium, wherein the co-aggregate comprises
  (i) a plurality of magnetic particles, each having a stimuli-responsive polymer attached thereto, and
  (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
wherein the co-aggregate is formed by the association of the stimuli-responsive polymer attached to the magnetic particle to the stimuli-responsive polymer attached to the non-magnetic particle;

(c) subjecting the co-aggregate to a magnetic field to magnetophorese the co-aggregate to a site within the liquid medium to provide a magnetophoresced co-aggregate in the liquid medium;

(d) removing at least portion of the liquid medium from the liquid medium comprising the magnetophoresced co-aggregate to provide the co-aggregate and optionally residual liquid medium;

(e) removing the stimulus and the magnetic field to provide a mixture comprising
  (i) a plurality of magnetic particles, each having a stimuli-responsive polymer attached thereto,
  (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
  (iii) optionally residual liquid medium.

In a further embodiment, the invention provides a method for capturing a diagnostic target in a liquid medium. The method includes the steps of:

(a) contacting a liquid medium to be tested for the presence of a diagnostic target with a first binding partner having an affinity to the diagnostic target and plurality of stimuli-responsive particles, wherein the plurality of stimuli-responsive particles comprises
  (i) a plurality of magnetic particles, each having a stimuli-responsive polymer attached thereto, and
  (ii) a plurality of non-magnetic particles, each having a stimuli-responsive polymer and a second binding partner attached thereto, wherein the second binding partner has an affinity to the first binding partner,
  wherein the plurality of stimuli-responsive particles is contacted with the liquid medium for a pre-determined period of time sufficient to effect binding of the diagnostic target, if present, to a portion of the plurality of non-magnetic particles through the association of the first and second binding partners;
(b) applying an external stimulus to provide a co-aggregate in the liquid medium, wherein the co-aggregate comprises
  (i) a plurality of magnetic particles, each having a stimuli-responsive polymer attached thereto, and
  (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
  wherein the co-aggregate is formed by the association of the stimuli-responsive polymer attached to the magnetic particle to the stimuli-responsive polymer attached to the non-magnetic particle;
(c) subjecting the co-aggregate to a magnetic field to magnetophorese the co-aggregate to a site within the liquid medium to provide a magnetophoresced co-aggregate in the liquid medium;
(d) removing at least portion of the liquid medium from the liquid medium comprising the magnetophoresced co-aggregate to provide the co-aggregate and optionally residual liquid medium;
(e) removing the stimulus and the magnetic field to provide a mixture comprising
  (i) a plurality of magnetic particles, each having a stimuli-responsive polymer attached thereto,
  (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
  (iii) optionally residual liquid medium.

In other aspects, the invention provides particles and systems for carrying out the methods.

DESCRIPTION OF THE DRAWINGS

The patent or application file contains at least one drawing executed in color. Copies of this patent or patent application publication with color drawings will be provided by the Office upon request and payment of the necessary fees.

The foregoing aspects and many of the attendant advantages of this invention will become more readily appreciated as the same become better understood by reference to the following detailed description, when taken in conjunction with the accompanying drawings.

FIG. 7A is an image of the flow strip. FIG. 7B is a graph comparing intensity as a function of streptavidin amount spiked into 50% human plasma samples were captured at a fixed sample volume of 200 µL. The background-subtracted mean pixel intensity (mean±SD, (n=3)) at the leading edge of the anti-streptavidin IgG binding patch on the nitrocellulose membrane was measured using Image J.

were processed using the AuNP/mNP bioseparation method. 500 µL of 50% human plasma containing the nanoparticle reagents, but no streptavidin (500, 0 SA) served as the negative control.

Figure 9:
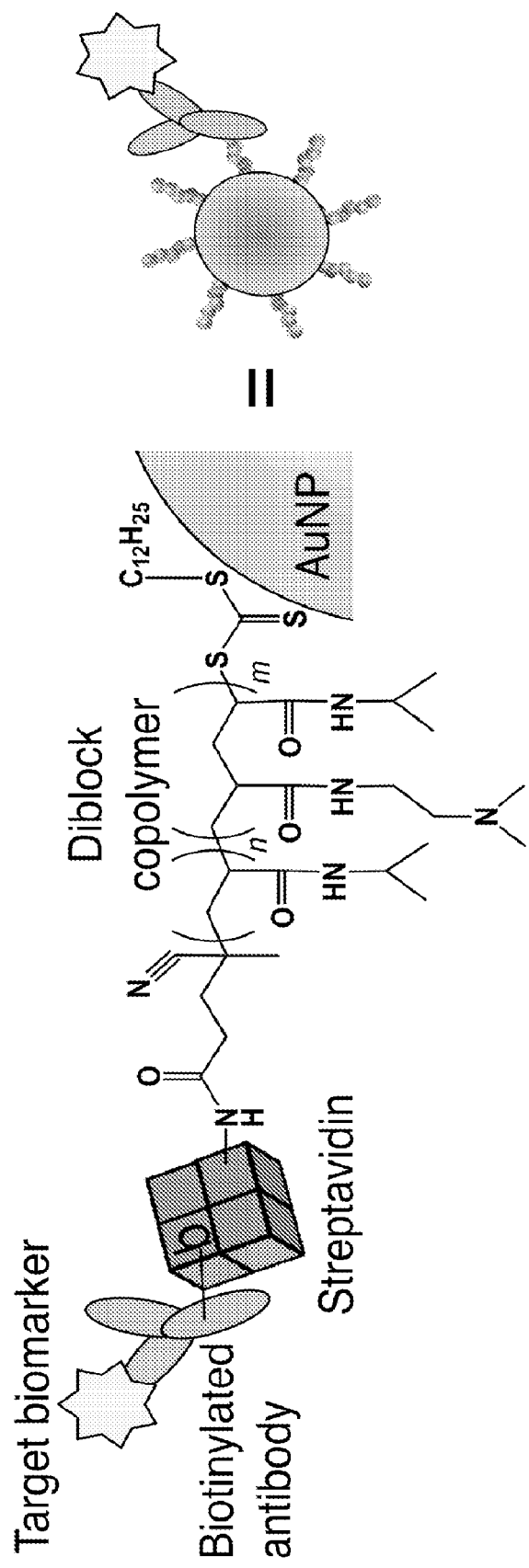

FIG. 9 is a schematic illustration of a representative non-magnetic particle useful in the practice of the methods of the invention for capturing a biomarker. In this embodiment, gold nanoparticles were modified with a diblock copolymer that binds via dual chemisorption and electrostatic mechanisms. The semi-telechelic carboxyl group on the polymer was conjugated to lysine groups on streptavidin, which bound to the complementary biotin groups on the antibody. This universal bioconjugate design allowed for facile multiplexing by simply adding multiple different biotinylated antibodies to the sample before addition of the universal streptavidin-gold reagent.

Figure 10:
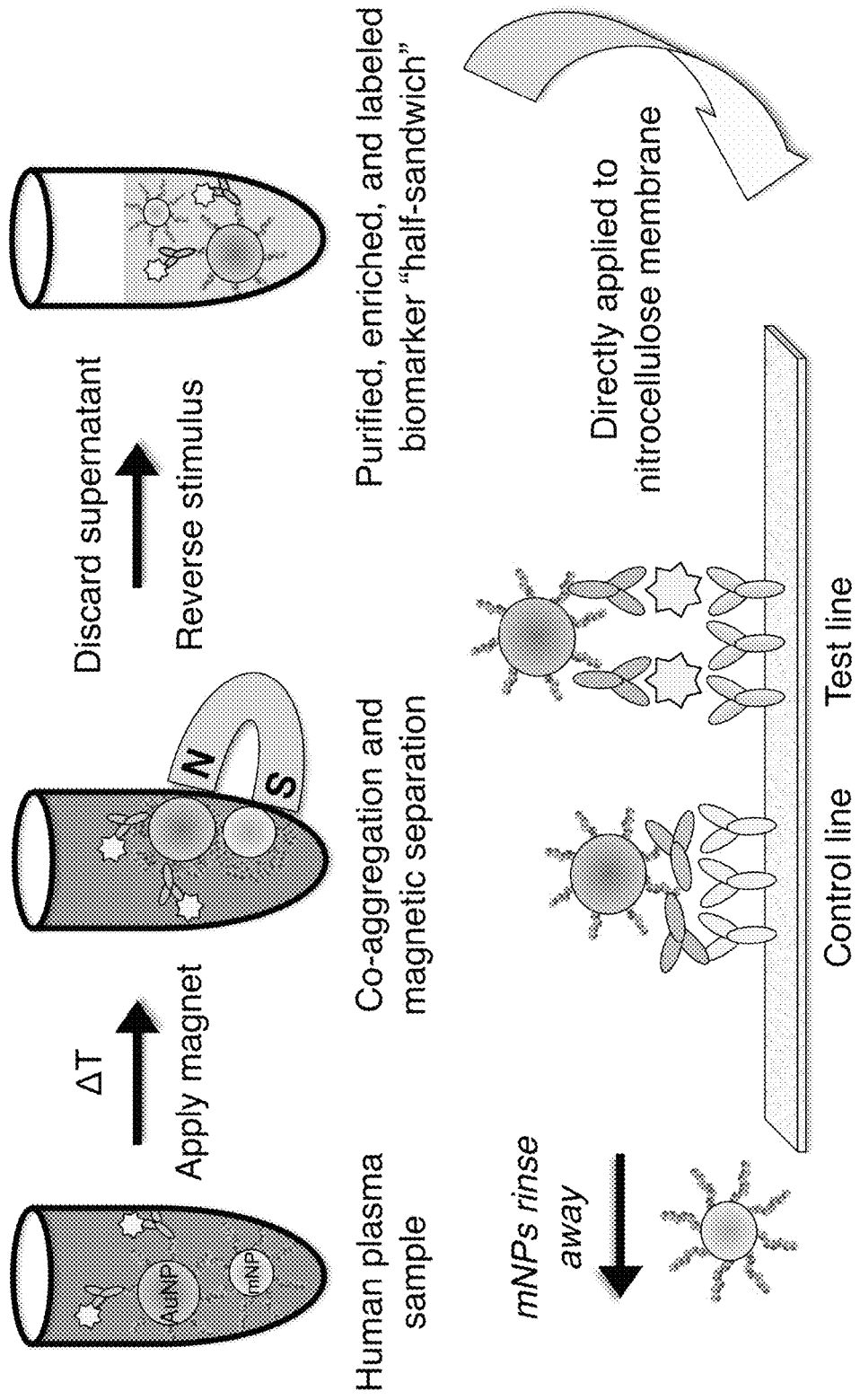

FIG. 10 is a schematic representation of a representative method of the invention, a magnetic enrichment lateral flow immunoassay. The biotinylated antibody was added to a plasma sample containing the target biomarker(s). The streptavidin-pNIPAAm-gold reagent was added, followed by the pNIPAAm magnetic nanoparticles and optionally free pNIPAAm polymer. When the sample was heated, the mixed AuNP/mNP particle aggregates were separated by a magnet. After discarding the supernatant, the captured aggregates were re-dissolved into a smaller volume cold buffer resulting in particle disaggregation and 50-fold enrichment. The enriched mixture was then applied directly to a lateral flow membrane with functionalized test and control line antibody regions.

Figure 11:
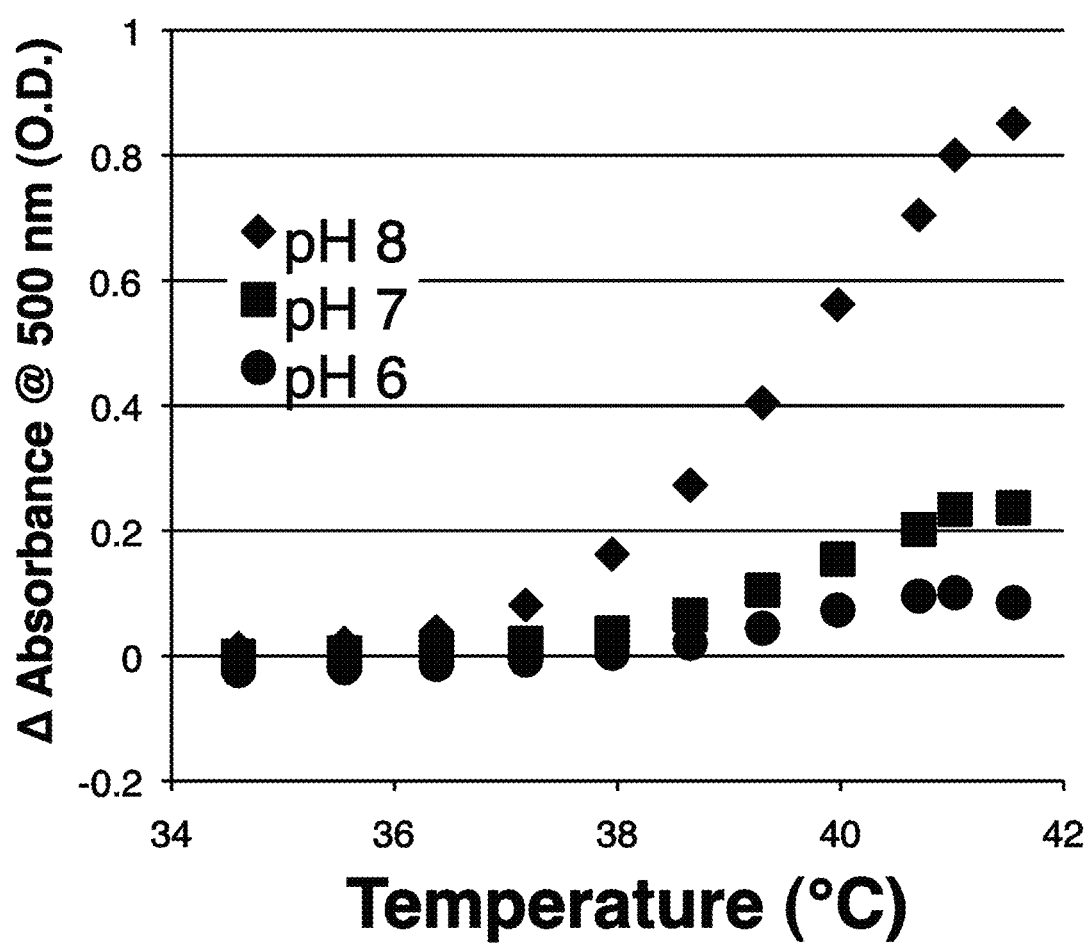

FIG. 11 illustrates the thermal aggregation profile as a function of pH for a representative diblock copolymer useful in the methods of the invention. The diblock copolymer light scattering was monitored in non-equilibrium mode where the sample temperature was ramped from room temperature to 45° C. in six minutes while simultaneously acquiring absorbance and temperature data. The polymer sample included 2 mg/mL of the 21.5 kDa diblock copolymer in 1×PBS buffer. Protonation of the amine groups of the polymer at pH 6 and 7 resulted in electrostatic repulsions that prevented strong aggregation and light scattering that was observed at pH 8.

Figure 12:
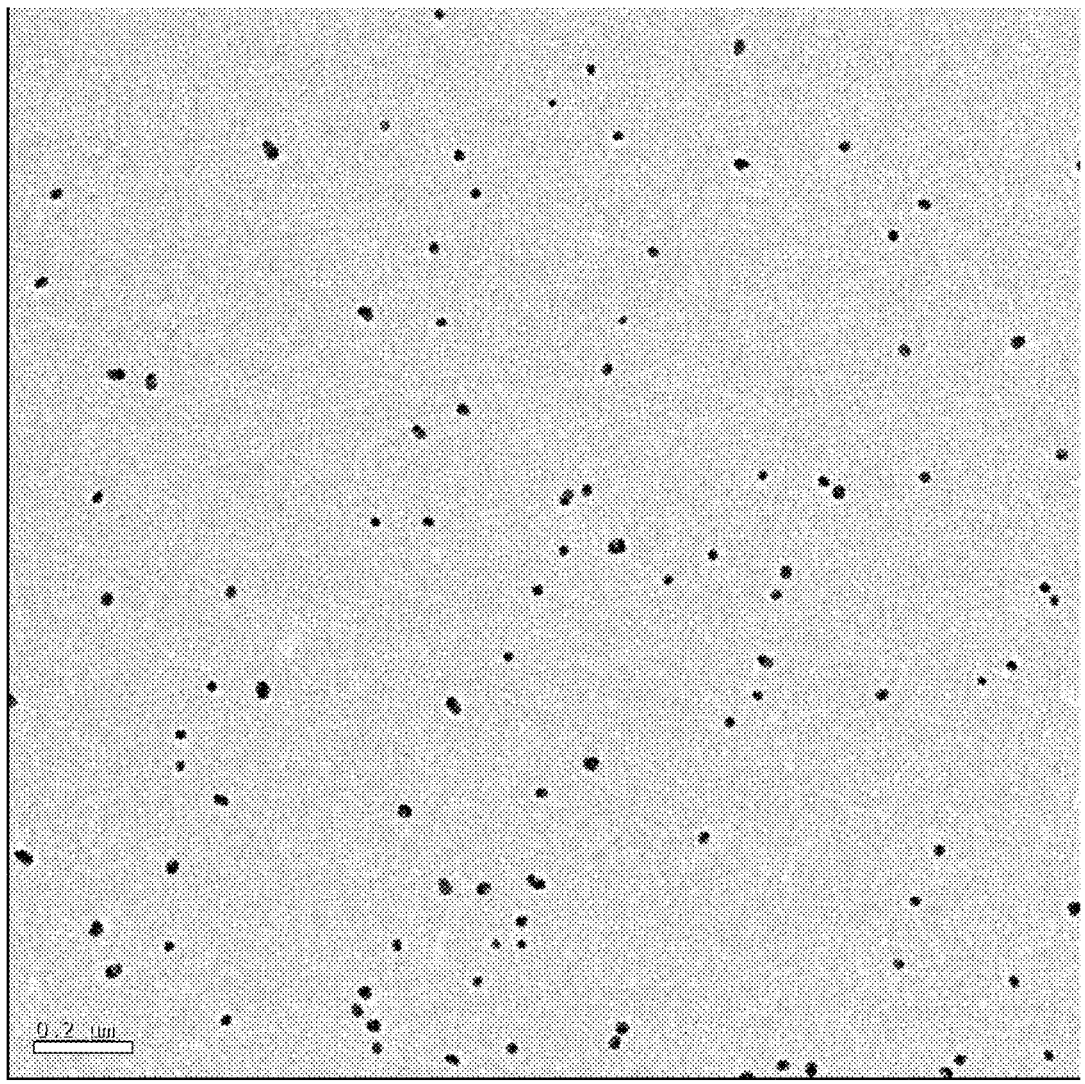

FIG. 12 is a transmission electron micrograph (200 kV) of representative citrate-reduced AuNPs useful in the methods of the invention. The AuNPs were aerosolized onto carbon stabilized formvar coated copper grids (Ted Pella) prior to analysis. Scale bar 200 nm.

Figure 13:
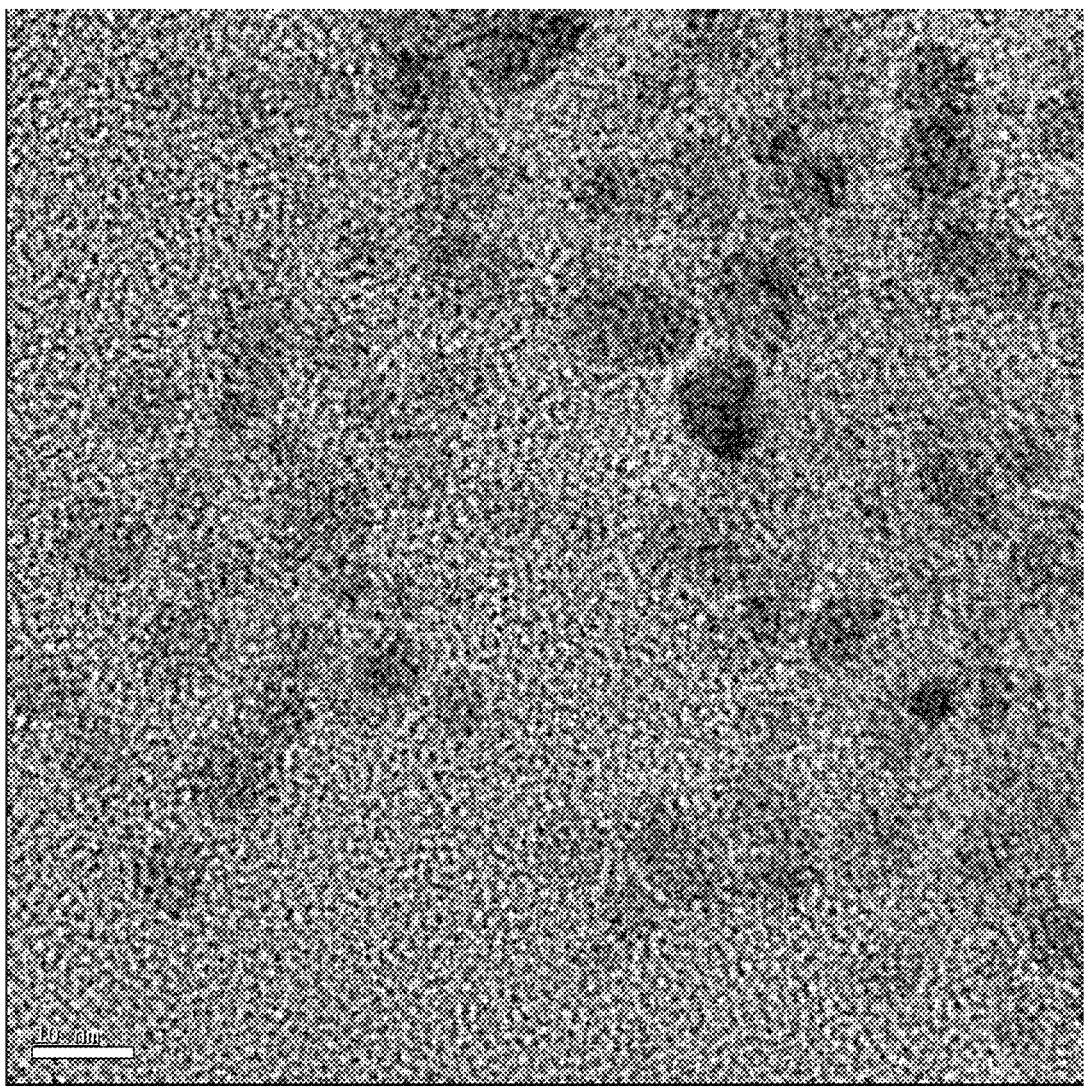

FIG. 13 is a transmission electron micrograph (200 kV) of representative pNIPAAm-mNPs useful in the methods of the invention. Scale bar 10 nm.

Figure 14:
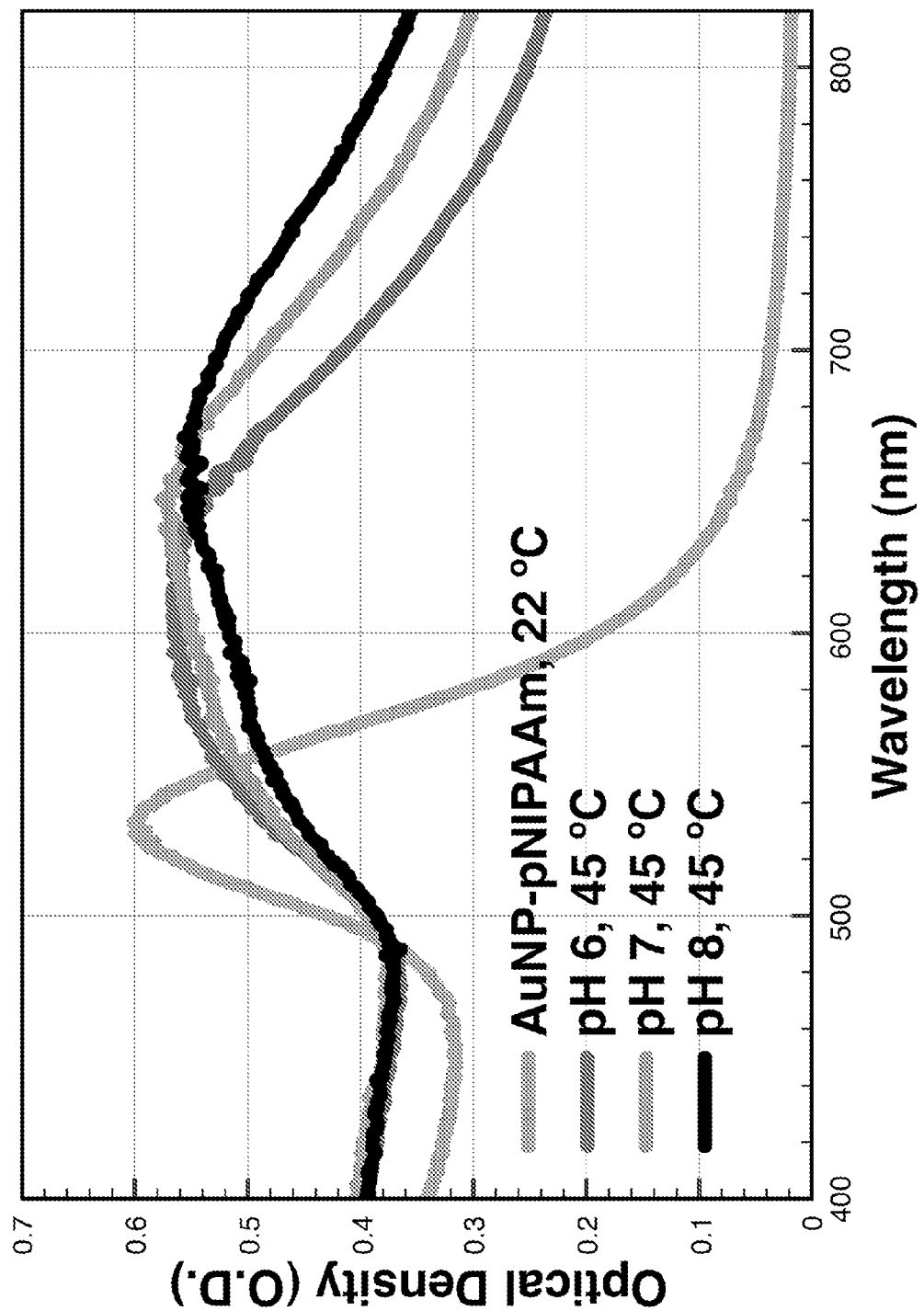

FIG. 14 compares red shifting of localized surface plasmon resonance of a representative diblock copolymer-modified AuNPs useful in the methods of the invention caused by thermally triggered aggregation. The AuNPs were dissolved at about 0.6 nM in PBS buffer and heated from room temperature to 45° C. in fifteen minutes. Less plasmonic coupling is observed at pH 6 than at pH 8. The amine groups are protonated at pH 6 resulting in electrostatic repulsion between AuNPs that prevent aggregation to a greater extent as compared with pH 8 when more amine groups are uncharged.

Figure 15:
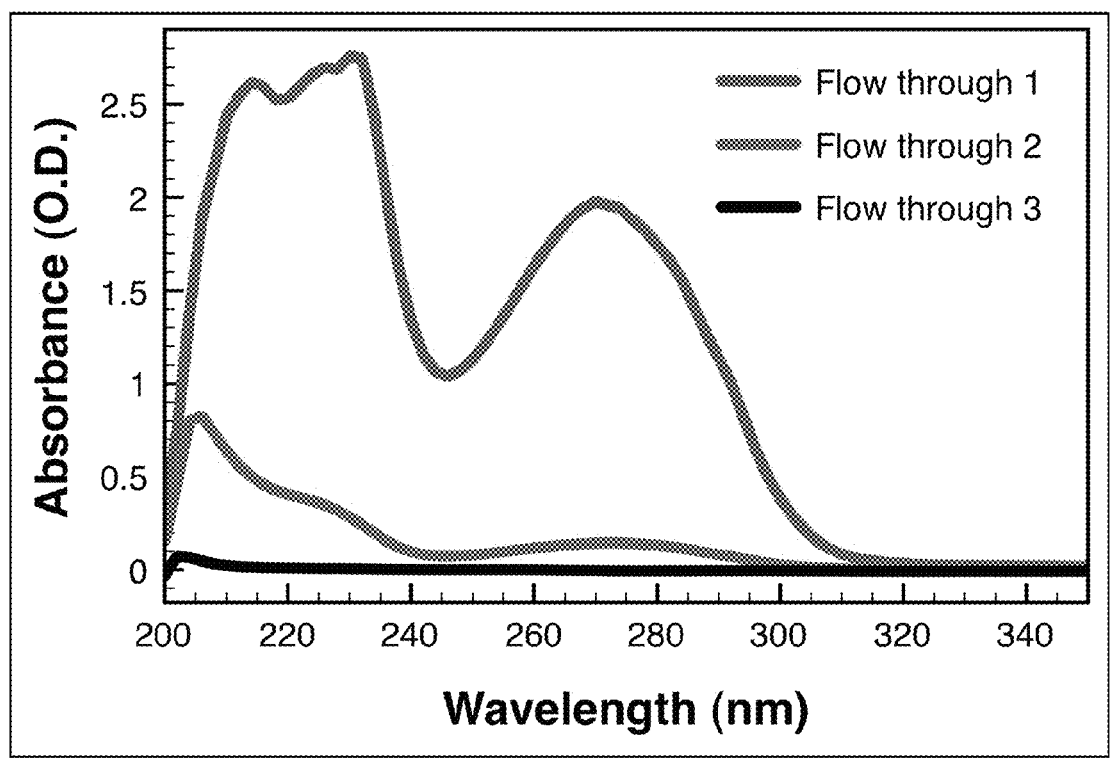

FIG. 15 compares the removal of non-conjugated streptavidin from streptavidin-AuNPs. After conjugation of a diblock copolymer-modified AuNPs to streptavidin, the non-conjugated streptavidin was removed by ultrafiltration using a cellulose membrane with a nominal molecular weight cut-off of 100 kDa. The absorbance at 280 nm was monitored during each subsequent round of ultrafiltration until no A280 was observed.

Figure 16:
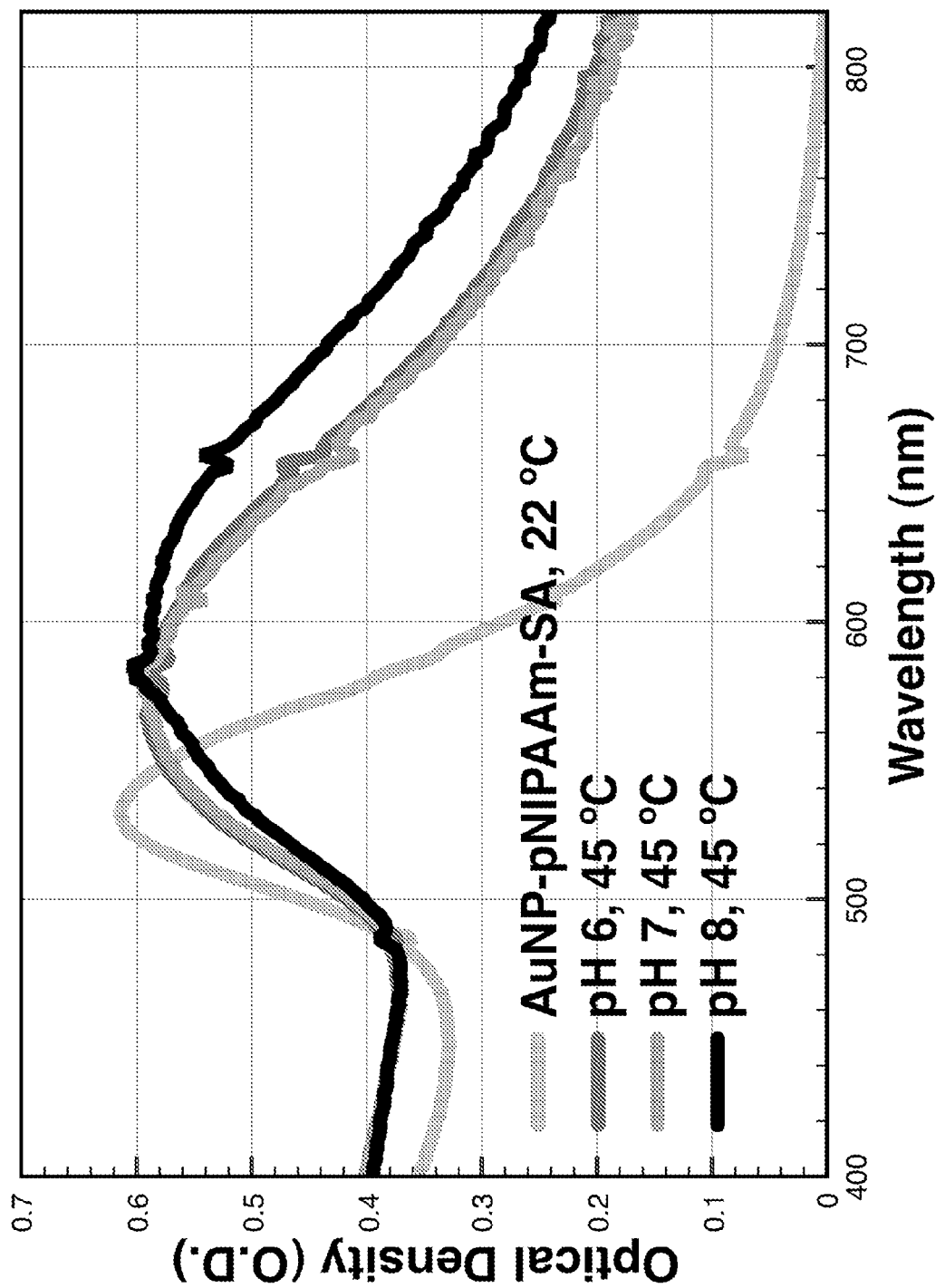

FIG. 16 compares red shifting of localized surface plasmon resonance of streptavidin-conjugated AuNPs (SA-AuNPs) useful in the methods of the invention caused by thermally triggered aggregation. After removal of non-conjugated streptavidin, the SA-AuNPs were dissolved at about 0.6 nM in PBS buffer and heated from room temperature to 45° C. in fifteen minutes. The thermally triggered aggregation of the SA-AuNPs shows the same pH dependence as the pNIPAAm-AuNPs and the polymer. However, the overall coupling of the LSPR is inhibited as compared with pNIPAAm-AuNPs. This is attributed to an increased hydrophilic protein mass at the particle surface preventing close aggregation of the AuNPs.

Figure 17A:
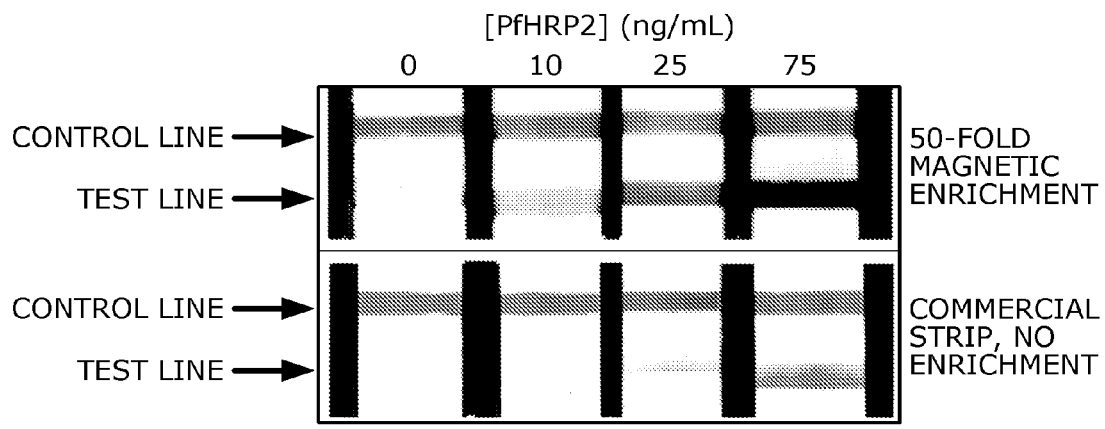
Figure 17B:
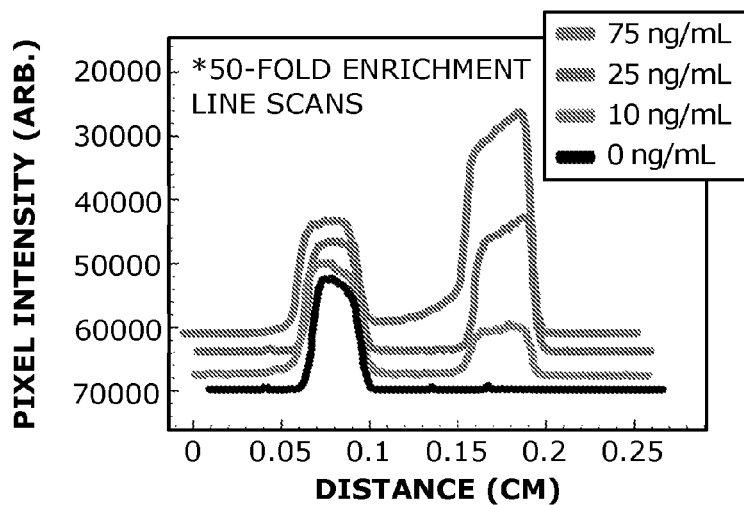
Figure 17C:
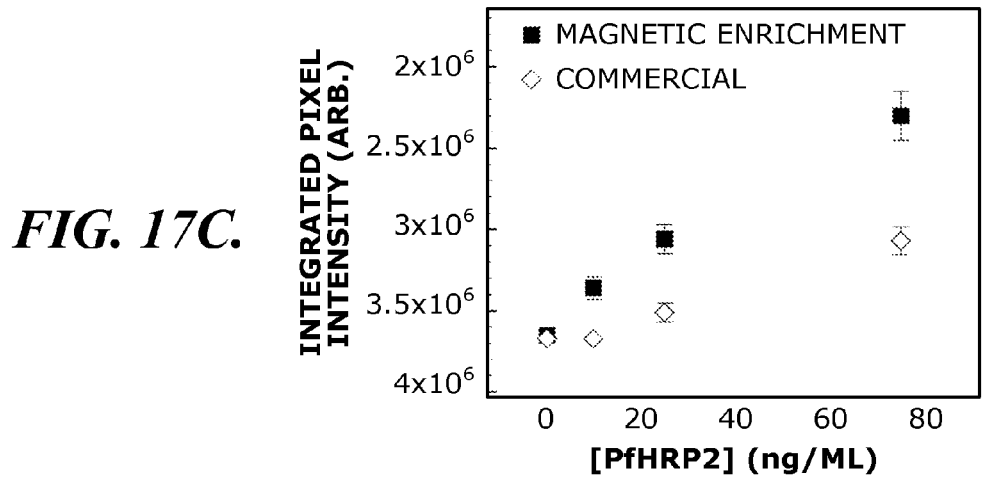

FIGS. 17A-17C illustrate representative magnetic enrichment lateral flow immunoassay results and comparison with commercial assay. FIG. 17A, top row: after 50-fold magnetic enrichment, the purified gold-labeled PfHRP2 biomarker was applied to the flow strip and rinsed. FIG. 17A, bottom row: the unmodified commercial lateral flow assay was performed on an equal volume of 50% human plasma containing the same initial biomarker concentration. FIG. 17B: green channel pixel intensities from the scanned images in FIG. 17A (top row) were plotted vs. distance along the strip. A leading edge of binding is observed on the upstream side of the test line located at x=0.17 cm. The control line was centered at x=0.08 cm, with fluid flow in the negative x direction. Line scans were offset for clarity. FIG. 17C: the integrated pixel intensity at the test line was plotted (mean±SD, n=3) for the commercial and magnetically enriched particle systems.

Figure 18A:
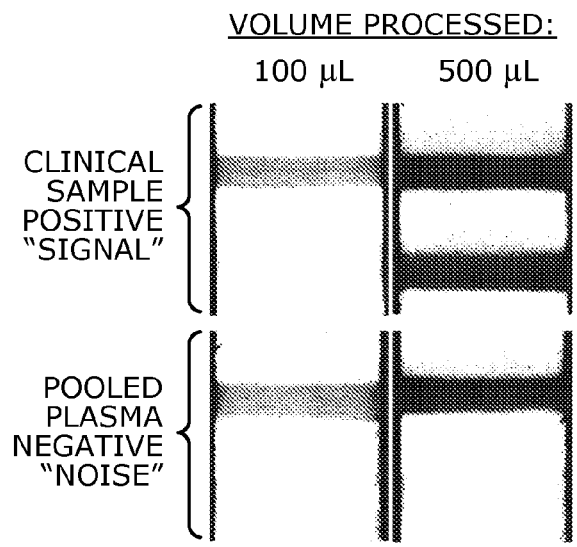
Figure 18B:
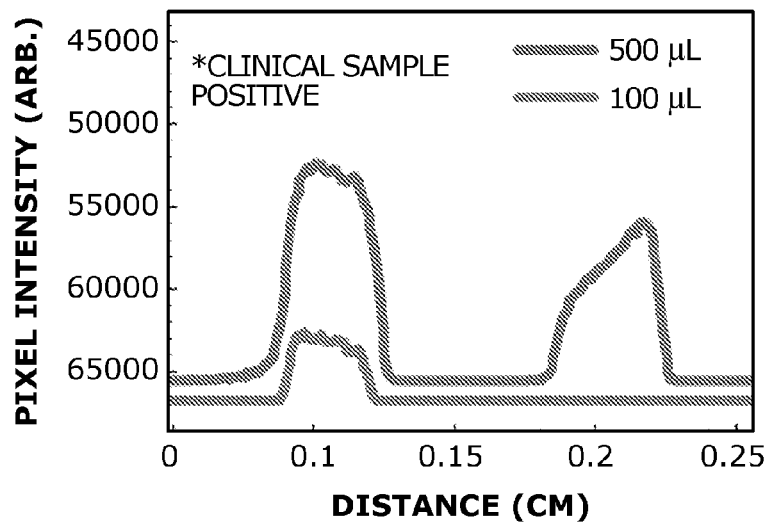
Figure 18C:
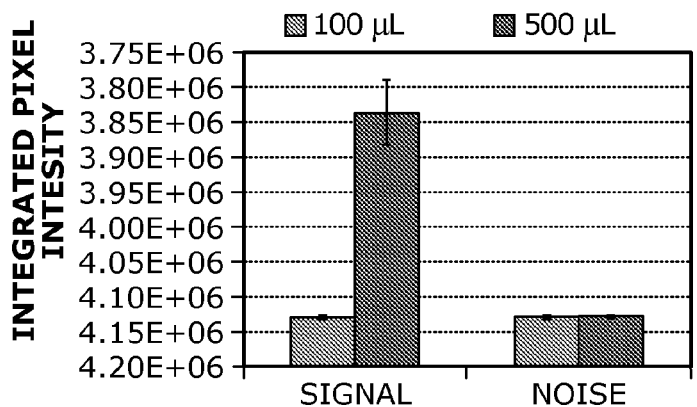

FIGS. 18A-18C illustrate the effect of increasing sample volume on assay signal and noise. The clinically-derived PfHRP2 antigen was spiked into pooled human plasma and magnetically enriched from 100 or 500 µL volumes down to 10 µL, representing 10 or 50-fold volumetric enrichment, respectively. For a 100 µL processed volume, the magnetic enrichment immunoassay resulted in a false negative test result (FIG. 18A, top left), while for the 500 µL of processed sample (FIG. 18A, top right) a strong signal (true positive) at the test line was observed. The assay noise, meanwhile, remained very low at each volume processed (FIG. 18A, bottom). FIG. 18B are line scans from the clinical sample positive, offset for clarity. FIG. 18C compares the integrated pixel intensity at the test line (mean±SD, n=3) for the clinical sample positive ("Signal") and pooled plasma negative ("Noise").

Figure 19:
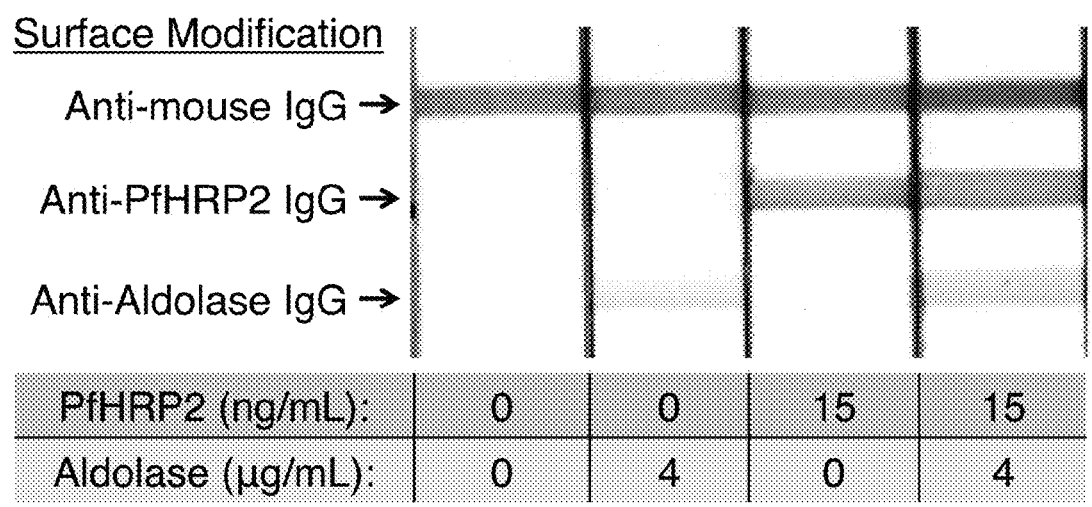

FIG. 19 illustrates the results for a representative multiplexed magneto-enrichment immunoassay of the invention. After binding of the biotinylated anti-PfHRP2 and anti-aldolase IgG antibodies to the PfHRP2 and aldolase mixed antigens in human plasma, the universal streptavidin gold reagent was added, followed by magnetic enrichment and lateral flow analysis. The bottom blue panel shows the respective concentrations of biomarkers in the original 500 µL sample.

DETAILED DESCRIPTION OF THE INVENTION

The present invention provides systems and methods for capturing, magnetically concentrating, and detecting biomarkers. The systems and methods achieve rapid magnetic separation of a non-magnetic particle biomarker in a simple mixture of separate stimuli-responsive particles where each can be optimized independently. The invention demonstrates that magnetic particles (e.g., pNIPAAm-mNPs) capture non-magnetic particles (e.g., pNIPAAm-AuNPs) through a co-aggregation mechanism, so that the thermally-triggered and high-efficiency enrichment of the non-magnetic particle bearing the captured biomarker (e.g., Au-labeled biomarker) to be used in lateral flow assay is achieved in a single step. The size of the co-aggregates are sufficient to rapidly magnetophorese toward the applied magnet. This strategy for purification and enrichment circumvents the high dose "hook" effect that can occur when excess sample biomarker occupies all of the binding sites on the solid-phase. This effect confounds lateral flow assays (e.g. lateral flow immunoassays, LFIAs) through lower signal strength at high biomarker concentrations. Magnetic separation eliminates the high dose "hook" effect because only biomarkers bound to the label (e.g., non-magnetic particle) are separated and applied to the flow strip. Magnetic separation/enrichment of the non-magnetic particle biomarkers from larger plasma volumes not only increase the sensitivity of LFIA, but could also eliminate sample-matrix-derived interferences.

In one aspect, the invention provides a method for concentrating a non-magnetic particle in a liquid.

In one embodiment, the method includes applying a magnetic field to a mixture comprising a co-aggregate in a liquid to provide a collected co-aggregate in the liquid, wherein the co-aggregate comprises (1) a magnetic particle having a stimuli-responsive polymer attached thereto, and (2) a non-magnetic particle having a stimuli-responsive polymer attached thereto. In the method, the co-aggregate is formed by the association of the stimuli-responsive polymer attached to the magnetic particle to the stimuli-responsive polymer attached to the non-magnetic particle. By use of the magnetic field, the co-aggregate is magnetophoresced such that the co-aggregate is collected or substantially isolated from the liquid medium In one embodiment, the co-aggregate further comprises free stimuli-responsive polymer. In this embodiment, the free polymer assists in co-aggregate formation by providing addition polymer associations.

The non-magnetic particle binds the diagnostic target (e.g., biomarker) that may be present in liquid sample. In one embodiment, the non-magnetic particle further comprises a first binding partner of a binding pair. The first binding partner is effective for binding a second binding partner. The first binding partner and the second binding partner are a binding pair. The liquid sample includes second binding partner. The terms "diagnostic target" and "second binding partner" are used interchangeably in this embodiment.

When the liquid includes a diagnostic target (i.e., a positive sample), the co-aggregate includes a non-magnetic particle having the first and second binding partners attached thereto (i.e., the non-magnetic particle has the diagnostic target bound to the particle through the interaction of the first binding partner and the diagnostic target).

In one embodiment, the first binding partner is an antibody and the second binding partner is an antigen. In one embodiment, the first binding partner is an antigen and the second binding partner is an antibody.

In one embodiment, the method further includes removing at least a portion of the liquid from the liquid medium comprising the collected co-aggregate. Removing at least a portion the liquid results in the co-aggregate (including bound diagnostic target) being concentrated or enriched relative to the original liquid sample. In certain embodiments, the liquid is substantially completed removed to provide the co-aggregate, optionally including residual liquid.

For further analysis, in one embodiment, the method includes re-dissolving the co-aggregate to provide a mixture comprising a magnetic particle having a stimuli-responsive polymer attached thereto and a non-magnetic particle having a stimuli-responsive polymer and first and second binding partners attached thereto. In one embodiment, re-dissolving the co-aggregate comprises removing the stimuli causing the association of the stimuli-responsive polymer attached to the magnetic particle to the stimuli-responsive polymer attached to the non-magnetic particle. Re-dissolving the co-aggregate can also include adding a liquid (e.g., buffer) to the co-aggregate. Removal of the stimulus and magnetic field (and optionally adding a liquid) provides a mixture that includes the magnetic particle having attached stimuli-responsive polymer and the non-magnetic particle having attached stimuli-responsive polymer with bound diagnostic target (i.e., first and second binding partners attached thereto), when the liquid sample includes the diagnostic target.

The diagnostic target captured by the method can be assayed. In one embodiment, the method further includes contacting a solid phase effective to immobilize the non-magnetic particle with the mixture including the magnetic particle having attached stimuli-responsive polymer and the non-magnetic particle having attached stimuli-responsive polymer and diagnostic target. In this embodiment, the solid phase includes a binding partner (e.g. antibody) attached thereto effective to bind the second binding partner (diagnostic target) to immobilize the non-magnetic particle. Suitable solid phases include porous solid phases (e.g., membranes or lateral flow devices) capable of wicking the liquid sample containing the bound diagnostic target. The solid phase can also be an array capable of detecting multiple diagnostic targets.

In certain embodiments, the method further includes determining the presence of the second binding partner (e.g., diagnostic target) in the liquid by observing the solid phase immobilization of the non-magnetic particle having a stimuli-responsive polymer and first and second binding partners attached thereto.

Figure 1:
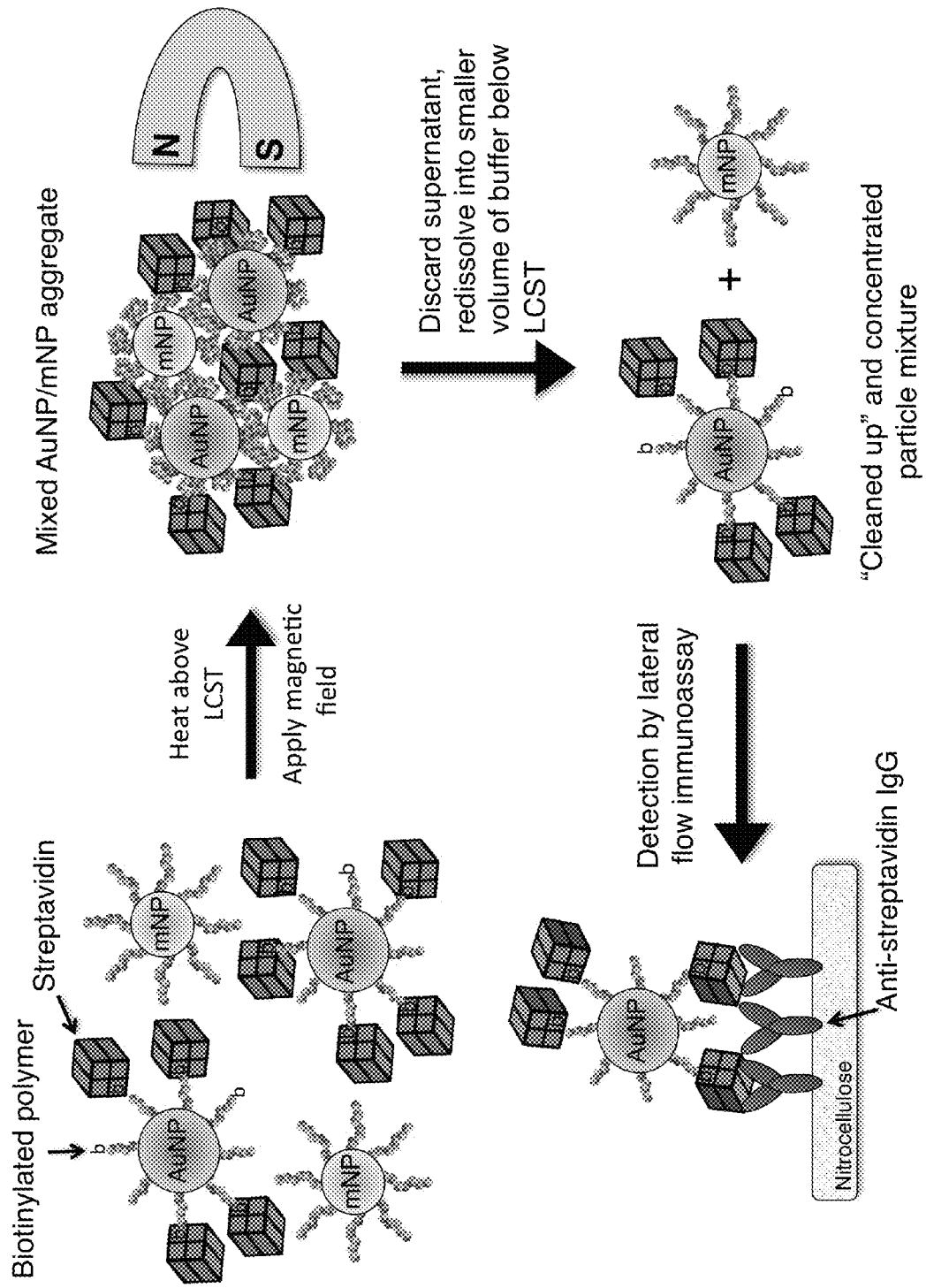
FIG. 1 is a schematic representation of a representative method of the invention. AuNPs coated with biotinylated diblock copolymers bind to streptavidin spiked into 50% human plasma. mNPs coated with homo-pNIPAAm are added, and the temperature is raised above the polymer LCST. Mixed streptavidin-AuNP/mNP aggregates are separated by a magnet. The separated aggregates with gold-labeled target protein are re-suspended into a smaller volume of buffer below the LCST, and flowed through an LFIA strip with immobilized capture antibodies. Visualization of the target protein is achieved by AuNP light extinction at the capture line of the LFIA strip, while the non-biofunctional mNPs are rinsed away.

FIG. 1 is a schematic illustration of a representative method of the invention.

The systems and methods of the invention include a non-magnetic particle bearing a stimuli-responsive polymer. Representative non-magnetic particles included colorimetric particles, fluorescent particles, enzyme-conjugated particles, radio-labeled particles, and Raman-active particles, each of which is readily detected in an assay format. Suitable non-magnetic particles include gold particles, silver particles, copper particles, latex particles, quantum dots, and semiconductor particles.

The systems and methods of the invention also include a magnetic particle bearing a stimuli-responsive polymer. Suitable magnetic particles are particles that are responsive to a magnetic field and magnetophorese through a medium in response to the application of a magnetic field. Representative magnetic particles include particles that include a suitable metal or metal oxide. Suitable metals and metal oxides include iron, nickel, cobalt, iron platinum, zinc selenide, ferrous oxide, ferric oxide, cobalt oxide, aluminum oxide, germanium oxide, tin dioxide, titanium dioxide, gadolinium oxide, indium tin oxide, cobalt iron oxide, magnesium iron oxide, manganese iron oxide, and mixtures thereof.

As noted above, each of the magnetic particle and the non-magnetic particle bears a stimuli-responsive polymer. The presence of the stimuli-responsive polymer provides for the formation of the co-aggregate on the application of an appropriate stimulus. For example, when the magnetic and non-magnetic particles bear a thermally-responsive polymer, the co-aggregate is formed by heating the liquid to a temperature above the lower critical solution temperature of the thermally-responsive polymer (e.g., a polymer comprising N-isopropylacrylamide repeating units, an N-isopropylacrylamide polymer or copolymer). When the magnetic and non-magnetic particles bear a pH-responsive polymer, the co-aggregate is formed by adjusting the pH of the liquid to a pH that causes the polymers to become associative (e.g., a polymer comprising acrylic acid or alkylacrylic acid repeating units, an acrylic acid or alkylacrylic acid polymer or copolymer). A representative pH-responsive polymer is an N-isopropylacrylamide/methylacrylic acid/tert-butyl methacrylate copolymer such as poly(N-isopropylacrylamide-co-methylacrylic acid-co-tert-butyl methacrylate. When the magnetic and non-magnetic particles bear an ionic strength-responsive polymer, the co-aggregate is formed by adjusting the ionic strength of the liquid such that the polymers become associative. Similarly, when the magnetic and non-magnetic particles bear a light-responsive polymer, the co-aggregate is formed by irradiating the liquid with a wavelength of light effective to cause the polymers to become associative.

Stimuli-responsive polymers. The particles useful in the systems and methods of the invention include stimuli-responsive polymers. In one embodiment, the stimuli-responsive polymers form a corona. As used herein, the term "corona" refers to the sphere or coating of stimuli-responsive polymers surrounding the particle core.

The stimuli-responsive polymer can be any polymer having a stimuli-responsive property. The stimuli-responsive polymer can be any one of a variety of polymers that change their associative properties (e.g., change from hydrophilic to hydrophobic) in response to a stimulus. The stimuli-responsive polymer responds to changes in external stimuli such as the temperature, pH, light, photo-irradiation, exposure to an electric field, ionic strength, and the concentration of certain chemicals by exhibiting property change. For example, a thermally-responsive polymer is responsive to changes in temperature by exhibiting a LCST in aqueous solution. The stimuli-responsive polymer can be a multi-responsive polymer, where the polymer exhibits property change in response to combined simultaneous or sequential changes in two or more external stimuli.

The stimuli-responsive polymers may be synthetic or natural polymers that exhibit reversible conformational or physico-chemical changes such as folding/unfolding transitions, reversible precipitation behavior, or other conformational changes to in response to stimuli, such as to changes in temperature, light, pH, ions, or pressure. Representative stimuli-responsive polymers include temperature-sensitive polymers (also referred to herein as "temperature-responsive polymers" or "thermally-responsive polymers"), pH-sensitive polymers (also referred to herein as "pH-responsive polymers"), and light-sensitive polymers (also referred to herein as "light-responsive polymers").

Stimulus-responsive polymers useful in making the particles described herein can be any which are sensitive to a stimulus that causes significant conformational changes in the polymer. Illustrative polymers described herein include temperature-, pH-, ion- and/or light-sensitive polymers. Hoffman, A. S., "Intelligent Polymers in Medicine and Biotechnology", *Artif. Organs.* 19:458-467, 1995; Chen, G. H. and A. S. Hoffman, "A New Temperature- and Ph-Responsive Copolymer for Possible Use in Protein Conjugation", *Macromol. Chem. Phys.* 196:1251-1259. 1995; Irie, M. and D. Kungwatchakun, "Photoresponsive Polymers. Mechanochemistry of Polyacrylamide Gels Having Triphenylmethane Leuco Derivatives", *Makromol. Chem., Rapid Commun.* 5:829-832, 1985; and Irie, M., "Light-induced Reversible Conformational Changes of Polymers in Solution and Gel Phase", *ACS Polym. Preprints*, 27(2):342-343, 1986; which are incorporated by reference herein.

Stimuli-responsive oligomers and polymers useful in the particles described herein can be synthesized that range in molecular weight from about 1,000 to 30,000 Daltons. In one embodiment, these syntheses are based on the chain transfer-initiated free radical polymerization of vinyl-type monomers, as described herein, and by (1) Tanaka, T., "Gels", *Sci. Amer.* 244:124-138. 1981; (2) Osada, Y. and S. B. Ross-Murphy, "Intelligent Gels", *Sci. Amer,* 268:82-87, 1993; (3) Hoffman, A. S., "Intelligent Polymers in Medicine and Biotechnology", *Artif. Organs* 19:458-467, 1995; also *Macromol. Symp.* 98:645-664, 1995; (4) Feijen, J., et al., "Thermosensitive Polymers and Hydrogels Based on N-isopropylacrylamide", 11*th European Conf. on Biomtls:*256-260, 1994; (5) Monji, N. and A. S. Hoffman, "A Novel Immunoassay System and Bioseparation Process Based on Thermal Phase Separating Polymers", *Appl. Biochem. and Biotech.* 14:107-120, 1987; (6) Fujimura, M., T. Mori and T. Tosa, "Preparation and Properties of Soluble-Insoluble Immobilized Proteases", *Biotech. Bioeng.* 29:747-752, 1987; (7) Nguyen, A. L. and J. H. T. Luong, "Synthesis and Applications of Water-Soluble Reactive Polymers for Purification and Immobilization of Biomolecules", *Biotech. Bioeng.* 34:1186-1190, 1989; (8) Taniguchi, M., et al., "Properties of a Reversible Soluble-Insoluble Cellulase and Its Application to Repeated Hydrolysis of Crystalline Cellulose", *Biotech. Bioeng.* 34:1092-1097, 1989; (9) Monji, N., et al., "Application of a Thermally-Reversible Polymer-Antibody Conjugate in a Novel Membrane-Based Immunoassay", *Biochem. and Biophys. Res. Comm.* 172:652-660, 1990; (10) Monji, N.C. A. Cole, and A. S. Hoffman, "Activated, N-Substituted Acrylamide Polymers for Antibody Coupling: Application to a Novel Membrane-Based Immunoassay", *J. Biomtls. Sci. Polymer Ed.* 5:407-420, 1994; (11) Chen, J. P. and A. S. Hoffman, "Polymer-Protein Conjugates: Affinity Precipitation of Human IgG by Poly(N-Isopropyl Acrylamide)-Protein A Conjugates", *Biomtls.* 11:631-634, 1990; (12) Park, T. G. and A. S. Hoffman, "Synthesis and Characterization of a Soluble, Temperature-Sensitive Polymer-Conjugated Enzyme, *J. Biomtls. Sci. Polymer Ed.* 4:493-504, 1993; (13) Chen, G. H., and A. S. Hoffman, Preparation and Properties of Thermo-Reversible, Phase-Separating Enzyme-Oligo(NIPAAm) Conjugates", *Bioconj. Chem.* 4:509-514, 1993; (14) Ding, Z. L., et al., "Synthesis and Purification of Thermally-Sensitive Oligomer-Enzyme Conjugates of Poly(NIPAAm)-Trypsin", *Bioconj. Chem.* 7: 121-125, 1995; (15) Chen, G. H. and A. S. Hoffman, "A New Temperature- and pH-Responsive Copolymer for Possible Use in Protein Conjugation", *Macromol. Chem. Phys.* 196:1251-1259, 1995; (16) Takei, Y. G., et al., "Temperature-responsive Bioconjugates. 1. Synthesis of Temperature-Responsive Oligomers with Reactive End Groups and their Coupling to Biomolecules", *Bioconj. Chem.* 4:42-46, 1993; (17) Takei, Y. G., et al., "Temperature-responsive Bioconjugates. 2. Molecular Design for Temperature-modulated Bioseparations", *Bioconj. Chem.* 4:341-346, 1993; (18) Takei, Y. G., et al., "Temperature-responsive Bioconjugates. 3. Antibody-Poly(N-isopropylacrylamide) Conjugates for Temperature-Modulated Precipitations and Affinity Bioseparations", *Bioconj. Chem.* 5:577-582, 1994; (19) Matsukata, M., et al., "Temperature Modulated Solubility-Activity Alterations for Poly(N-Isopropylacrylamide)-Lipase Conjugates", *J. Biochem.* 116:682-686, 1994; (20) Chilkoti, A., et al., "Site-Specific Conjugation of a Temperature-Sensitive Polymer to a Genetically-Engineered Protein", *Bioconj. Chem.* 5:504-507, 1994; and (21) Stayton, P. S., et al., "Control of Protein-Ligand Recognition Using a Stimuli-Responsive Polymer", *Nature* 378:472-474, 1995.

The stimuli-responsive polymers useful in the particles include homopolymers and copolymers having stimuli-responsive behavior. Other suitable stimuli-responsive polymers include block and graft copolymers having one or more stimuli-responsive polymer components. A suitable stimuli-responsive block copolymer may include, for example, a temperature-sensitive polymer block, or a pH-sensitive block. A suitable stimuli-responsive graft copolymer may include, for example, a pH-sensitive polymer backbone and pendant temperature-sensitive polymer components, or a temperature-sensitive polymer backbone and pendant pH-sensitive polymer components.

The stimuli-responsive polymer can include a polymer having a balance of hydrophilic and hydrophobic groups, such as polymers and copolymers of N-isopropylacrylamide. An appropriate hydrophilic/hydrophobic balance in a smart vinyl type polymer is achieved, for example, with a pendant hydrophobic group of about 2-6 carbons that hydrophobically bond with water, and a pendant polar group such as an amide, acid, amine, or hydroxyl group that H-bond with water. Other polar groups include sulfonate, sulfate, phosphate and ammonium ionic groups. Preferred embodiments are for 3-4 carbons (e.g., propyl, isopropyl, n-butyl, isobutyl, and t-butyl) combined with an amide group (e.g. PNIPAAm), or 2-4 carbons (e.g., ethyl, propyl, isopropyl, n-butyl, isobutyl, and t-butyl) combined with a carboxylic acid group (e.g., PPAA). There is also a family of smart A-B-A (also A-B-C) block copolymers of polyethers, such as PLURONIC polymers having compositions of PEO-PPO-PEO, or polyester-ether compositions such as PLGA-PEG-PLGA. In one embodiment, the stimuli-responsive polymer is a temperature responsive polymer, poly(N-isopropylacrylamide) (PNIPAAm).

The stimuli-responsive polymer useful in the invention can be a smart polymer having different or multiple stimuli responsivities, such as homopolymers responsive to pH or light. Block, graft, or random copolymers with dual sensitivities, such as pH and temperature, light and temperature, or pH and light, may also be used. Thermally-Responsive Polymers. Illustrative embodiments of the many different types of thermally-responsive polymers that may be conjugated to interactive molecules are polymers and copolymers of N-isopropyl acrylamide (NIPAAm). PolyNIPAAm is a thermally-responsive polymer that precipitates out of water at 32° C., which is its lower critical solution temperature (LCST), or cloud point (Heskins and Guillet, *J. Macromol. Sci.-Chem.* A2:1441-1455, 1968). When polyNIPAAm is copolymerized with more hydrophilic comonomers such as acrylamide, the LCST is raised. The opposite occurs when it is copolymerized with more hydrophobic comonomers, such as N-t-butyl acrylamide. Copolymers of NIPAAm with more hydrophilic monomers, such as AAm, have a higher LCST, and a broader temperature range of precipitation, while copolymers with more hydrophobic monomers, such as N-t-butyl acrylamide, have a lower LCST and usually are more likely to retain the sharp transition characteristic of PNIPAAm (Taylor and Cerankowski, *J. Polymer Sci.* 13:2551-2570, 1975; Priest et al., *ACS Symposium Series* 350:255-264, 1987; and Heskins and Guillet, *J. Macromol. Sci.-Chem.* A2:1441-1455, 1968, the disclosures of which are incorporated herein). Copolymers can be produced having higher or lower LCSTs and a broader temperature range of precipitation.

Thermally-responsive oligopeptides also may be incorporated into the particles.

pH-Responsive Polymers. Synthetic pH-responsive polymers useful in making the particles described herein are typically based on pH-sensitive vinyl monomers, such as acrylic acid (AAc), methacrylic acid (MAAc) and other alkyl-substituted acrylic acids such as ethylacrylic acid (EAAc), propylacrylic acid (PAAc), and butylacrylic acid (BAAc), maleic anhydride (MAnh), maleic acid (MAc), AMPS (2-acrylamido-2-methyl-1-propanesulfonic acid), N-vinyl formamide (NVA), N-vinyl acetamide (NVA) (the last two may be hydrolyzed to polyvinylamine after polymerization), aminoethyl methacrylate (AEMA), phosphoryl ethyl acrylate (PEA) or methacrylate (PEMA). pH-Responsive polymers may also be synthesized as polypeptides from amino acids (e.g., polylysine or polyglutamic acid) or derived from naturally-occurring polymers such as proteins (e.g., lysozyme, albumin, casein), or polysaccharides (e.g., alginic acid, hyaluronic acid, carrageenan, chitosan, carboxymethyl cellulose) or nucleic acids, such as DNA. pH-Responsive polymers usually contain pendant pH-sensitive groups such as —OPO$(OH)_2$, —COOH, or —$NH_2$ groups. With pH-responsive polymers, small changes in pH can stimulate phase-separation, similar to the effect of temperature on solutions of PNIPAAm (Fujimura et al. *Biotech. Bioeng.* 29:747-752 (1987)). By randomly copolymerizing a thermally-sensitive NIPAAm with a small amount (e.g., less than 10 mole percent) of a pH-sensitive comonomer such as AAc, a copolymer will display both temperature and pH sensitivity. Its LCST will be almost unaffected, sometimes even lowered a few degrees, at pHs where the comonomer is not ionized, but it will be dramatically raised if the pH-sensitive groups are ionized. When the pH-sensitive monomer is present in a higher content, the LCST response of the temperature-sensitive component may be "eliminated" (e.g., no phase separation seen up to and above 100° C.).

Graft and block copolymers of pH and temperature-sensitive monomers can be synthesized that retain both pH and temperature transitions independently. Chen, G. H., and A. S. Hoffman, *Nature* 373:49-52, 1995. For example, a block copolymer having a pH-sensitive block (polyacrylic acid) and a temperature-sensitive block (PNIPAAm) can be useful in the invention.

Light-Responsive Polymers. Light-responsive polymers usually contain chromophoric groups pendant to or along the main chain of the polymer and, when exposed to an appropriate wavelength of light, can be isomerized from the trans to the cis form, which is dipolar and more hydrophilic and can cause reversible polymer conformational changes. Other light sensitive compounds can also be converted by light stimulation from a relatively non-polar hydrophobic, non-ionized state to a hydrophilic, ionic state.

In the case of pendant light-sensitive group polymers, the light-sensitive dye, such as aromatic azo compounds or stilbene derivatives, may be conjugated to a reactive monomer (an exception is a dye such as chlorophyllin, which already has a vinyl group) and then homopolymerized or copolymerized with other conventional monomers, or copolymerized with temperature-sensitive or pH-sensitive monomers using the chain transfer polymerization as described above. The light sensitive group may also be conjugated to one end of a different (e.g., temperature) responsive polymer. A number of protocols for such dye-conjugated monomer syntheses are known.

Although both pendant and main chain light sensitive polymers may be synthesized and are useful for the methods and applications described herein, the preferred light-sensitive polymers and copolymers thereof are typically synthesized from vinyl monomers that contain light-sensitive pendant groups. Copolymers of these types of monomers are prepared with "normal" water-soluble comonomers such as acrylamide, and also with temperature- or pH-sensitive comonomers such as NIPAAm or AAc.

Light-sensitive compounds may be dye molecules that isomerize or become ionized when they absorb certain wavelengths of light, converting them from hydrophobic to hydrophilic conformations, or they may be other dye molecules which give off heat when they absorb certain wavelengths of light. In the former case, the isomerization alone can cause chain expansion or collapse, while in the latter case the polymer will precipitate only if it is also temperature-sensitive.

Light-responsive polymers usually contain chromophoric groups pendant to the main chain of the polymer. Typical chromophoric groups that have been used are the aromatic diazo dyes (Ciardelli, *Biopolymers* 23:1423-1437, 1984; Kungwatchakun and Irie, *Makromol. Chem., Rapid Commun.* 9:243-246, 1988; Lohmann and Petrak, *CRC Crit. Rev. Therap. Drug Carrier Systems* 5:263, 1989; Mamada et al., *Macromolecules* 23:1517, 1990, each of which is incorporated herein by reference). When this type of dye is exposed to 350-410 nm UV light, the trans form of the aromatic diazo dye, which is more hydrophobic, is isomerized to the cis form, which is dipolar and more hydrophilic, and this can cause polymer conformational changes, causing a turbid polymer solution to clear, depending on the degree of dye-conjugation to the backbone and the water solubility of the main unit of the backbone. Exposure to about 750 nm visible light will reverse the phenomenon. Such light-sensitive dyes may also be incorporated along the main chain of the backbone, such that the conformational changes due to light-induced isomerization of the dye will cause polymer chain conformational changes. Conversion of the pendant dye to a hydrophilic or hydrophobic state can also cause individual chains to expand or contract their conformations. When the polymer main chain contains light sensitive groups (e.g., azo benzene dye) the light-stimulated state may actually contract and become more hydrophilic upon light-induced isomerization. The light-sensitive polymers can include polymers having pendant or backbone azobenzene groups.

Specific Ion-Responsive Polymers. Polysaccharides, such as carrageenan, that change their conformation, for example, from a random to an ordered conformation, as a function of exposure to specific ions, such as potassium or calcium, can also be used as the stimulus-responsive polymers. In another example, a solution of sodium alginate may be gelled by exposure to calcium. Other specific ion-sensitive polymers include polymers with pendant ion chelating groups, such as histidine or EDTA.

Polymers that are responsive to changes in ionic strength can also be used.

Dual- or Multi-Responsive Polymers. If a light-responsive polymer is also thermally responsive, the UV- or visible light-stimulated conversion of a chromophore conjugated along the backbone to a more hydrophobic or hydrophilic conformation can also stimulate the dissolution or precipitation of the copolymer, depending on the polymer composition and the temperature. If the dye absorbs the light and converts it to thermal energies rather than stimulating isomerization, then the localized heating can also stimulate a phase change in a temperature-sensitive polymer such as PNIPAAm, when the system temperature is near the phase separation temperature. The ability to incorporate multiple sensitivities, such as temperature and light sensitivity, or temperature and pH sensitivity, along one backbone by vinyl monomer copolymerization lends great versatility to the synthesis and properties of the responsive polymer-protein conjugates. For example, dyes can be used which bind to protein recognition sites, and light-induced isomerization can cause loosening or detachment of the dye from the binding pocket (Bieth et al., *Proc. Natl. Acad. Sci. USA* 64:1103-1106, 1969). This can be used for manipulating affinity processes by conjugating the dye to the free end of a temperature responsive polymer, such as ethylene oxide-propylene oxide (EO-PO) random copolymers available from Carbide. These polymers, —$(CH_2CH_2O)_x$—$(CH_2CHCH_3O)_y$—, have two reactive end groups. The phase separation point (cloud point) can be varied over a wide range, depending on the EO/PO ratio, molecular weight, and concentration, and one end may be derivatized with the ligand dye and the other end with an —SH reactive group, such as vinyl sulfone (VS).

Binding Partners and Binding Pairs. In the systems and methods of the invention, the non-magnetic particles include functionality to capture the diagnostic target from a liquid sample. The non-magnetic particle can include a capture moiety for directly capturing the diagnostic target. Alternatively, the non-magnetic particle can include a functional group that can be used to capture the diagnostic target indirectly. In one embodiment, the non-magnetic particle includes a first binding partner. A first binding partner has an affinity to a second binding partner. In one embodiment, the first binding partner is a capture moiety and the second binding partner is the diagnostic target. In another embodiment, the first binding partner is an avidin and the second binding partner is a biotinylated material (e.g., having affinity to the diagnostic target).

As used herein, the term "diagnostic target" refers to a molecule that is indicative of a diseased condition, an indicator of exposure to a toxin, or a therapeutic drug that has been administered to a subject and whose concentration is to be monitored. In one embodiment, the diagnostic target is a biomarker.

The diagnostic target can be any protein, antibody, or nucleic acid related to a disease. In one embodiment, the diagnostic target is an antibody against hepatitis B virus. In one embodiment, the diagnostic target is an antibody against hepatitis C virus. In one embodiment, the diagnostic target is an antibody against AIDS virus. In one embodiment, the diagnostic target is the malaria parasitic antigen, or the antiplasmodial antibodies, or the parasitic metabolic products, or the plasmodia nucleic acid fragments. In one embodiment, the diagnostic target is an antibody against tuberculosis bacteria. In one embodiment, the diagnosis target is a dengue fever virus or antibody.

In one embodiment, the diagnostic target is an antibody and the capture moiety is an antigen. In one embodiment, the diagnostic target is an antigen and the capture moiety is an antibody. In one embodiment, the diagnostic target is a nucleic acid oligomer (RNA or DNA) and the capture moiety is a complementary nucleic acid oligomer. In one embodiment, the diagnostic target is a nucleic acid oligomer (RNA or DNA) and the capture moiety is a protein. In one embodiment, the diagnostic target is a protein and the capture moiety is a nucleic acid oligomer (RNA or DNA). In one embodiment, the diagnostic target is an enzyme and the capture moiety is a substrate. In one embodiment, the diagnostic target is an enzyme substrate and the capture moiety is an enzyme.

A capture molecule (e.g., capture moiety) and a target molecule (e.g., diagnostic target) form a binding pair. Each has an affinity toward the other (e.g., antigen and antibody). Each of the capture molecule and the target molecule can be a variety of different molecules, including peptides, proteins, poly- or oligosaccharides, glycoproteins, lipids and lipoproteins, and nucleic acids, as well as synthetic organic or inorganic molecules having a defined bioactivity, such as an antibiotic or anti-inflammatory agent, that binds to a target site, such as a cell membrane receptor. The exemplary proteins include antibodies (monoclonal, polyclonal, chimeric, single-chain or other recombinant forms), their protein/peptide antigens, protein/peptide hormones, streptavidin, avidin, protein A, protein G, growth factors and their respective receptors, DNA-binding proteins, cell membrane receptors, endosomal membrane receptors, nuclear membrane receptors, neuron receptors, visual receptors, and muscle cell receptors. Exemplary oligonucleotides include DNA (genomic or cDNA), RNA, antisense, ribozymes, and external guide sequences for RNAase P, and can range in size from short oligonucleotide primers up to entire genes. Carbohydrates include tumor associated carbohydrates (e.g., $Le^x$, sialyl $Le^x$, $Le^y$, and others identified as tumor associated as described in U.S. Pat. No. 4,971,905, incorporated herein by reference), carbohydrates associated with cell adhesion receptors (e.g., Phillips et al., Science 250:1130-1132, 1990), and other specific carbohydrate binding molecules and mimetics thereof which are specific for cell membrane receptors.

In one embodiment, the capture molecule is an antibody and the target molecule is an antigen. In another embodiment, both the capture molecule and the target molecule are protein. In another embodiment, the capture molecule is a nucleic acid (DNA or RNA) and the target molecule is a complimentary nucleic acid (DNA or RNA). In another embodiment, the target molecule is a nucleic acid (DNA or RNA) and the capture molecule is a protein. In another embodiment, the capture molecule is a cell membrane receptor and the target molecule is a ligand. In another embodiment, the capture moiety is an enzyme and the target molecule is a substrate. In another embodiment, the capture molecule is biotin and the target molecule is streptavidin or avidin conjugate of a diagnostic target. In another embodiment, the capture molecule is an avidin (e.g., streptavidin) and the target molecule is a biotinylated material effective for binding the diagnostic target.

Among the proteins, streptavidin is particularly useful as a model for other capture moiety-target molecule binding pair systems described herein., and also a component useful in many indirect separations and diagnostic technologies which use the very strong association of the streptavidin-biotin affinity complex. (Wilchek and Bayer, Avidin-Biotin Technology, New York, Academic Press, Inc., 1990; and Green, Meth. Enzymol. 184:51-67. Protein G, a protein that binds IgG antibodies (Achari et al., Biochemistry 31:10449-10457, 1992, and Akerstrom and Bjorck, J. Biol. Chem. 261:10240-10247, 1986) is also useful as a model system. Representative immunoaffinity molecules include engineered single chain Fv antibody (Bird et al., Science 242:423-426, 1988 and U.S. Pat. No. 4,946,778 to Ladner et al., incorporated herein by reference, Fab, Fab', and monoclonal or polyclonal antibodies.

As used herein, the term "avidin" refers to any biotin-binding protein other than an immunoglobulin that binds biotin including both natural proteins and recombinant and genetically engineered proteins. The term includes the two common biotin-binding proteins known as "egg white or avian avidin" and "streptavidin." Egg white or avian avidin, commonly referred to simply as avidin, is a protein that is a constituent of egg white and forms a noncovalent complex with biotin. Streptavidin is a protein isolated from the actinobacterium Streptomyces avidinii and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. The term also refers to avidin derivatives including succinyl avidin, ferritin avidin, enzyme avidin and crosslinked avidin. The term "biotin" refers to any one of a variety of biotin derivatives and analogs that are effective in avidin binding. Suitable biotin moieties include those moieties that enable the biotinylated peptide fragment to be isolated by avidin and related avidin proteins. Representative biotin moieties include biotin derivatives such as iminobiotin, biocytin, and caproylamidobiotin, and biotin analogs such as desthiobiotin and biotin sulfone.

Other binding pairs include conconavalin A, which has an affinity to sugars (e.g., mannose, glucose, and galactose).

Devices that utilize stimuli-responsive particles. In one aspect, the invention also provides devices for using the stimuli-responsive particle system.

In one embodiment, the invention provides a device, comprising (a) a channel adapted for receiving a flow comprising a plurality of stimulus-responsive non-magnetic and magnetic particles, wherein each particle is reversibly associative in response to a stimulus; and (b) a separation region through which the flow passes, wherein the separation region is adapted to reversibly apply a stimulus and a magnetic field to the flow to capture the particles.

In one embodiment, the device is a well of a multi-well plate. In one embodiment, the device is a fluidic device having a channel. In one embodiment, the device's channel further comprises a surface having an array or plurality of capture regions. As used herein, the term "capture region" refers to a region of the surface of the channel coated with a plurality of stimulus-responsive polymers for capturing the nanoparticles. In one embodiment, the separation region is non-fouling.

The device useful in the invention permits reversible, stimuli-induced aggregation of the stimuli-responsive particles followed by magnetic field-induced aggregation of the stimuli-induced aggregates.

The preparation and characterization of representative magnetic and non-magnetic particles useful in the methods of the invention are described in Example 1. The use of these particles in a representative method of the invention is also described in Example 1.

The results demonstrate enhancing the performance of rapid tests using the dual AuNP/mNP system to achieve rapid and integrated biomarker labeling, enrichment, and detection. An advantage of the system is the use of stimuli-responsive coatings to direct co-aggregation of two different types of nanoparticles, each with pre-designed functionalities. The mNPs enable separation/enrichment of the diagnostic target bound to the AuNPs when the aggregate size is large enough to achieve rapid magnetophoretic separations, while the AuNPs provide a high-efficiency absorbing species by which the target molecule is visualized without the need for advanced optical detectors.

System and Method for Capturing Diagnostic Targets from a Liquid Sample

In another aspect, the invention provides a system and method for capturing one or more diagnostic targets (e.g., biomarkers) from a liquid sample.

In one embodiment, the method comprises:

(a) contacting a liquid medium to be tested for the presence of a diagnostic target with a plurality of stimuli-responsive particles, wherein the plurality of stimuli-responsive particles comprises (i) a plurality of magnetic particles, each having a stimuli-responsive polymer attached thereto, and (ii) a plurality of non-magnetic particles, each having a stimuli-responsive polymer and a capture moiety attached thereto, wherein the capture moiety has an affinity to the diagnostic target, wherein the plurality of stimuli-responsive particles is contacted with the liquid medium for a pre-determined period of time sufficient to effect binding of the diagnostic target, if present, to a portion of the plurality of non-magnetic particles;

(b) applying an external stimulus to provide a co-aggregate in the liquid medium, wherein the co-aggregate comprises
   (i) a plurality of magnetic particles, each having a stimuli-responsive polymer attached thereto, and
   (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
   wherein the co-aggregate is formed by the association of the stimuli-responsive polymer attached to the magnetic particle to the stimuli-responsive polymer attached to the non-magnetic particle;

(c) subjecting the co-aggregate to a magnetic field to magnetophorese the co-aggregate to a site within the liquid medium to provide a magnetophoresced co-aggregate in the liquid medium;

(d) removing at least portion of the liquid medium from the liquid medium comprising the magnetophoresced co-aggregate to provide the co-aggregate and optionally residual liquid medium;

(e) removing the stimulus and the magnetic field to provide a mixture comprising
   (i) a plurality of magnetic particles, each having a stimuli-responsive polymer attached thereto,
   (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
   (iii) optionally residual liquid medium.

In one embodiment, the method further comprises contacting the mixture with a solid phase to immobilize at least a portion of the plurality of non-magnetic particles have the diagnostic target attached thereto. A representative solid phase is an immunochromatographic solid phase (e.g., LFIA). In one embodiment, the method further comprises determining the presence non-magnetic particles having the diagnostic target attached thereto on the solid phase.

The system and method of the invention are applicable to analyzing a liquid sample that includes more than one diagnostic target. In one embodiment, the liquid medium to be tested comprises a first and a second diagnostic target and the plurality of non-magnetic particles comprises
   (i) a plurality of first non-magnetic particles, each having a stimuli-responsive polymer and a first capture moiety attached thereto, wherein the first capture moiety has an affinity to the first diagnostic target, and
   (ii) a plurality of second non-magnetic particles, each having a stimuli-responsive polymer and a second capture moiety attached thereto, wherein the second capture moiety has an affinity to the second diagnostic target.

In this embodiment, the method further comprises contacting the mixture (magnetic particles and first and second non-magnetic particles having first and second diagnostic targets bounds thereto, respectively) with a solid phase to immobilize at least a portion of the first plurality of non-magnetic particles having the first diagnostic target attached thereto and to immobilize at least a portion of the second plurality of non-magnetic particles having the second diagnostic target attached thereto. In one embodiment, the non-magnetic particles having the first diagnostic target attached thereto are immobilized on the solid phase at a first position and the non-magnetic particles having the second diagnostic target attached thereto are immobilized on the solid phase at a second position, wherein the first and second positions are not the same.

It will be appreciated that the system and method of the invention are not limited to capturing, concentrating, and detecting only two diagnostic targets, as described above. The system and methods of the invention are applicable to capturing, concentrating, and detecting multiple diagnostic targets from a single sample by appropriate selection of capture moieties ultimately bound to the non-magnetic particles.

The nature of the diagnostic target captured, concentrated, and detected by the system and method of the invention is widely variable. In one embodiment, the diagnostic target is a biomarker for a disease or disorder. In one embodiment, the diagnostic target is a cancer biomarker. In one embodiment, the diagnostic target is prostate-specific antigen (PSA, prostate cancer), carcinoembryonic antigen (CEA, colorectal, breast, lung, or pancreatic cancer), or cancer antigen 125 (CA-125, ovarian cancer). In one embodiment, the diagnostic target is an HIV antigen or an HIV antibody. In one embodiment, diagnostic target is the HIV antigen p24. In one embodiment, the diagnostic target is PfHRP2 antigen or aldolase. In one embodiment, the diagnostic target is an IgM diagnostic of measles.

In another embodiment, the invention provides a system and method for capturing one or more diagnostic targets through the use of first and second binding partners (e.g., avidin:biotin) rather than through capture by direct attachment of a capture moiety to non-magnetic particle.

In one embodiment, the invention provides a method for capturing a diagnostic target in a liquid medium, comprising:
   (a) contacting a liquid medium to be tested for the presence of a diagnostic target with a first binding partner having an affinity to the diagnostic target and plurality of stimuli-responsive particles, wherein the plurality of stimuli-responsive particles comprises
      (i) a plurality of magnetic particles, each having a stimuli-responsive polymer attached thereto, and
      (ii) a plurality of non-magnetic particles, each having a stimuli-responsive polymer and a second binding partner attached thereto, wherein the second binding partner has an affinity to the first binding partner,
   wherein the plurality of stimuli-responsive particles is contacted with the liquid medium for a pre-determined period of time sufficient to effect binding of the diagnostic target, if present, to a portion of the plurality of non-magnetic particles through the association of the first and second binding partners;

(b) applying an external stimulus to provide a co-aggregate in the liquid medium, wherein the co-aggregate comprises
      (i) a plurality of magnetic particles, each having a stimuli-responsive polymer attached thereto, and
      (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
      wherein the co-aggregate is formed by the association of the stimuli-responsive polymer attached to the magnetic particle to the stimuli-responsive polymer attached to the non-magnetic particle;

(c) subjecting the co-aggregate to a magnetic field to magnetophorese the co-aggregate to a site within the liquid medium to provide a magnetophoresced co-aggregate in the liquid medium;

(d) removing at least portion of the liquid medium from the liquid medium comprising the magnetphoresced co-aggregate to provide the co-aggregate and optionally residual liquid medium;

(e) removing the stimulus and the magnetic field to provide a mixture comprising
  (i) a plurality of magnetic particles, each having a stimuli-responsive polymer attached thereto,
  (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
  (iii) optionally residual liquid medium.

In one embodiment, the method further comprises contacting the mixture with a solid phase to immobilize at least a portion of the plurality of non-magnetic particles have the diagnostic target attached thereto.

In one embodiment, the first binding partner is a biotinylated antibody having affinity for the diagnostic target and the second binding partner is an avidin (e.g., streptavidin). In another embodiment, the first binding partner is an avidin (e.g., streptavidin) conjugate of an antibody having affinity for the diagnostic target and the second binding partner is biotin.

In one embodiment, the method further comprises determining the presence non-magnetic particles have the diagnostic target attached thereto on the solid phase.

In one embodiment, the liquid medium includes first and second diagnostic targets. In the method, contacting the liquid medium comprises contacting with a first binding partner having an affinity to the first diagnostic target, a third binding partner having an affinity to the second diagnostic target, and plurality of stimuli-responsive particles, wherein the plurality of stimuli-responsive particles comprises
  (i) a plurality of magnetic particles, each having a stimuli-responsive polymer attached thereto,
  (ii) a plurality of first non-magnetic particles, each having a stimuli-responsive polymer and a second binding partner attached thereto, wherein the second binding partner has an affinity to the first binding partner, and
  (iii) a plurality of second non-magnetic particles, each having a stimuli-responsive polymer and a fourth binding partner attached thereto, wherein the fourth binding partner has an affinity to the third binding partner,
wherein the plurality of stimuli-responsive particles is contacted with the liquid medium for a pre-determined period of time sufficient to effect binding of the first and second diagnostic targets, if present, to a portion of the pluralities of the first and second non-magnetic particles through the association of the first and second, and third and fourth binding partners, respectively.

In one embodiment, the second and fourth binding partners are the same. In another embodiment, the second and fourth binding partners are different.

In one embodiment, the second and fourth binding partners are an avidin and the first and third binding partners are biotinylated antibodies. In another embodiment, the second and fourth binding partners are biotin and the first and third binding partners are avidin conjugates of antibodies.

In one embodiment, the method further comprises contacting the mixture with a solid phase to immobilize at least a portion of the plurality of first non-magnetic particles having the first diagnostic target attached thereto and to immobilize at least a portion of the plurality of second non-magnetic particles having the second diagnostic target attached thereto. In one embodiment, the non-magnetic particles having the first diagnostic target attached thereto are immobilized on the solid phase at a first position and the non-magnetic particles having the second diagnostic target attached thereto are immobilized on the solid phase at a second position, wherein the first and second positions are not the same.

The preparation and characterization of representative magnetic and non-magnetic particles useful in the multiplexed methods of the invention are described in Example 2. The use of these particles in a representative multiplexed method of the invention is also described in Example 2.

The results demonstrate that a representative mixed AuNP/mNP system achieves homogeneous capture, labeling, and strong volumetric enrichment of AuNP-biomarker half stacks. This is unlike conventional magnetic enrichment schemes, where the magnetic nanoparticle is conjugated to a targeting ligand and forms one side of the sandwich immunocomplex. Magnetophoresis was instead conferred to the AuNP-biomarker half stacks via the "smart" polymer surface coatings. Following enrichment, AuNP-biomarker half stacks were able to bind to another antibody at the immunospecific test line on the solid phase, forming a sandwich immunocomplex. The magnetic enrichment lateral flow immunoassay of the invention has relatively high sensitivity, around 10 ng/mL or better with clinically derived sample matrices, and is competitive with currently available commercial lateral flow and ELISA systems.

Coordination of a universal streptavidin-pNIPAAm-gold reagent with multiple biotinylated antibodies each with different specificities is shown to be advantageous for facile multiplexing of biomarker detection. With clinical malaria samples, the method of the invention demonstrates a 50-fold magneto-enrichment improvement in the signal of the immunochromatographic assay, without increasing the background noise. The method of the invention achieves homogeneous capture, labeling, purification, enrichment, and high-sensitivity detection of protein biomarkers from plasma in a non-instrumented and readily multiplexed format.

The following examples are provided for the purpose of illustrating, not limiting, the invention.

EXAMPLES

Materials

N,N-dimethylaminoethylacrylamide (DMAEAm; Monomer, Polymer, & Dajac Labs) was twice distilled through a short path prior to use. NIPAAm (Sigma, 97%) was recrystallized from hexanes prior to use. 2,2-Azobis(2-methylpropionitrile) (AIBN; Aldrich, 98%) was recrystallized from methanol. The RAFT chain transfer agent 4-cyano-4-(dodecylsulfanylthiocarbonyl)sulfanyl pentanoic acid (DCT) was synthesized as described in Moad, G., Chong, Y. K., Postma, A., Rizzardoi, E., and Thang, S. H. (2005) Advances in RAFT polymerization: the synthesis of polymers with defined end-groups. *Polymer* 46, 8458-8468. 2-(Dodecylsulfanylthiocarbonylsulfanyl)-2-methylpropionic acid (DMP) was a gift from Noveon. Dioxane (EMD, 99%), dimethylformamide (DMF; EMD, 99.8%), dichloromethane (DCM; EMD, 99.8%), pentane (J. T. Baker, 99%), tetraglyme (Aldrich, 99%), methanol (MeOH; EMD, 99.9%), tetrahydrofuran (THF; Mallinckrodt, 99.8%), N,N'-dicycohexylcarbodiimide (DCC; Fluka, 99%), 1-ethyl-3-[3-dimethylaminopropyl]carbodiimide hydrochloride (EDC; Pierce, 98%), N-hydroxysuccinimide (NHS; Fluka, 97%), HAuCl$_4$ (Aldrich, 99.99%), Fe(CO)$_5$ (Aldrich, 99.9%), and D-biotin (Aldrich, 99%) were used as received. Cellulose ultrafiltration membranes for AuNP purification were from Millipore (regenerated cellulose, 44.5 mm diameter, NMWL 100,000, Cat No: 14422AM) and PD-10 desalting columns were from GE Healthcare. NH$_2$—PEG$_2$-biotin, HABA biotin quantitation kit, and dialysis membranes (7 & 20 kDa MWCO) were purchased from Pierce. Streptavidin labeled with ALEX-AFLUOR 750 (SA-750 streptavidin) was purchased from Invitrogen. Purified rabbit polyclonal anti-streptavidin IgG was purchased from Abcam (Product No. Ab6676). 1× Phosphate buffered saline packets (1×PBS; 10 mM phosphate, 138 mM NaCl, 2.7 mM KCl, pH 7.4 at 25° C.) and 2-(N-morpholino)ethanesulfonic acid (100 mM MES, 100 mM NaCl) buffer packets were purchased from Sigma. Human rediscovered plasma in disodium EDTA (Valley Biomedical Inc., product No. HP1051) was centrifuged at 1000×g for 30 minutes and filtered through GDX graded syringe filters (Whatman) prior to use. Magnets were NdFeB, 5 cm×1.27 cm×0.63 cm, Br max=12.1 kGauss (Force Field Magnets.com). Nitrocellulose LFIA membranes were Millipore HiFlow Plus 180. Zymed non-specific membrane blocking solution was purchased from Invitrogen.

Example 1

Preparation and Characterization of Representative Magnetic and Non-Magnetic Particles and Their Use in a Representative Method of the Invention In this example, the preparation and characterization of representative magnetic and non-magnetic particles useful in the methods of the invention are described. The use of these particles in a representative method of the invention is also described.

System Design. The bioseparation/enrichment system consists of a mixture of magnetic and gold nanoparticles, each with a "smart" polymer coating. Gold nanoparticles (about 25 nm diameter) were modified with a biotinylated amine-containing diblock copolymer, and magnetic nanoparticles (about 10 nm diameter) were synthesized directly with a homo-pNIPAAm polymer surface coating. When mixtures of these two particle types were heated above the polymer LCST, the particles co-aggregated driven by hydrophobic interactions between the collapsed polymers. 8 kDa homo-pNIPAAm (2 mg/mL) was added to the particle mixture to facilitate mNP and AuNP cross-aggregation. The aggregates contained both magnetic (iron oxide) and gold aggregates with a strongly enhanced magnetophoretic mobility that allowed them to be rapidly co-separated in an applied magnetic field gradient. The separation mechanism is illustrated in FIG. 1. By re-suspending the magnetically captured particle aggregates into a smaller volume of fluid, the gold-labeled model target biomarker streptavidin could be concentrated many fold. The enriched gold-labeled target protein was then analyzed and visualized with an anti-streptavidin immunochromatographic flow strip.

Polymer Synthesis. RAFT polymerization was carried out using previously published procedures (Lai, J. J., Hoffman, J. M., Ebara, M., Hoffman, A. S., Estournes, C., Wattiaux, A., and Stayton, P. S. (2007) Dual magnetic-/temperature-responsive nanoparticles for microfluidic separations and assays. *Langmuir* 23, 7385-7391) with slight modification. A homo-pNIPAAm polymer with a target molecular weight of 15 kDa was polymerized by dissolving in a round bottom flask 2 grams (17.7 mmol) of NIPAAm, 54 mg (0.134 mmol) of DCT, and 2.2 mg (13.4 μmol) of AIBN in 4 grams p-dioxane. The flask was purged with N$_2$ for 30 minutes and heated at 60° C. for 12 hours, followed by precipitation into pentane. The product was dried under vacuum, dialyzed against DI water at 4° C., and freeze-dried. A 5 kDa homo-pNIPAAm for use in mNP synthesis was prepared by polymerization in a round bottom flask containing 2 grams (17.7 mmol) of NIPAAm, 143.3 mg (0.4 mmol) of DMP, 6.66 mg (40.5 μmol) of AIBN, and 4 grams of p-dioxane. Precipitation and purification was carried out identically as for the 15 kDa homo-pNIPAAm.

Diblock extension was performed by dissolving in a round-bottom flask 1.32 g (83 μmol) of the about 15 kDa homo-pNIPAAm mCTA, 0.2258 g (1.59 mmol) of DMAEAm, 0.18 g (1.59 mmol) of NIPAAm, 1.4 mg (8.3 μmol) of AIBN in 8 mL of MeOH. This resulted in a [DMAEAm]:[NIPAAm]:[mCTA]:[initiator] ratio of 18:18:1:0.1. The flask was purged with N$_2$ for 30 minutes, followed by heating at 60° C. for 18 hours. The MeOH was removed by rotary evaporation, and the product was dissolved in 5 mL of THF, and precipitated thrice into pentane. The precipitate was dried under vacuum, dissolved in DI water, purified by PD-10 desalting column, and freeze-dried.

Polymer Analysis. Polymers were characterized using GPC performed on an Agilent 1200 series liquid chromatography system equipped with TSKgel alpha 3000 and TSKgel alpha 4000 columns (TOSOH biosciences). The mobile phase was LiBr (0.01 M) in HPLC grade DMF at a flow rate of 1 mL/min. MALS data were obtained on a miniDAWN TREOS (Wyatt Technologies Corp.) with 658 nm laser source, and three detectors at 45.8°, 90.0°, and 134.2°. The instrument calibration constant was $5.746 \times 10^{-5}$ V$^{-1}$cm$^{-1}$. Refractive index was measured using an Optilab Rex detector (Wyatt Technologies Corp.). The dn/dc value for the homo-pNIPAAm macro-chain transfer agent (mCTA) was determined under the assumption of 100% mass recovery. The dn/dc value for the diblock copolymer was determined by injecting polymer samples at known concentrations into the RI detector post-column. The dn/dc value was then calculated using linear regression with the Astra 5.3.4.14 data analysis software package (Wyatt Technologies Corp.). $^1$H-NMR (300 MHz) spectroscopy in CDCl$_3$ was obtained on a Bruker AV300. Nanoparticle absorption was measured on a Hewlett Packard 8453 diode array extinction spectrophotometer in quartz cuvette sample holder. TEM was performed on a Technai G2 F20 200 kV microscope. Absorbance and fluorescence measurements were made using a 96-well microplate reader (Tecan)

Figure 2:
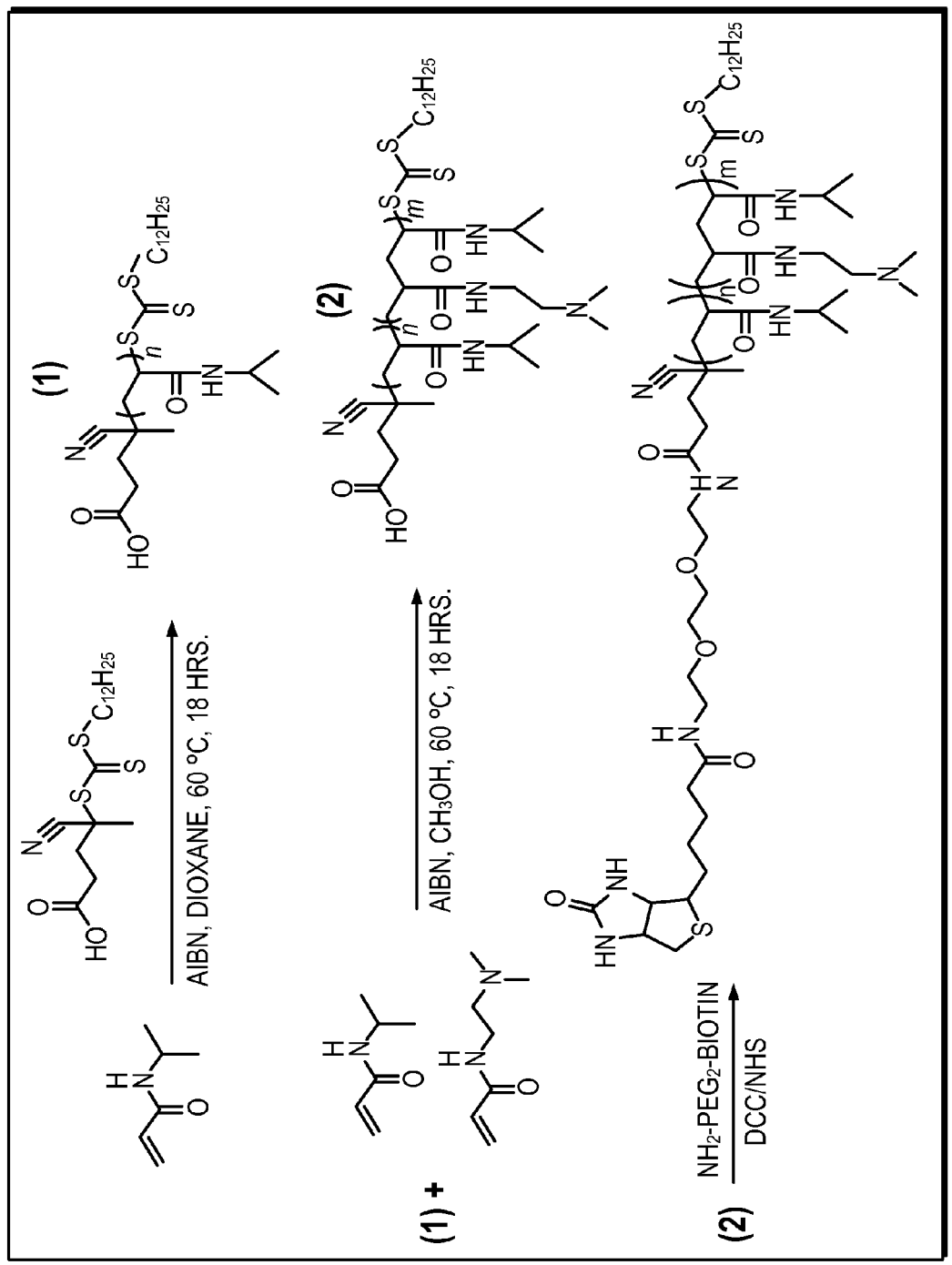
FIG. 2 is a schematic illustration of the preparation of a representative stimuli-responsive polymer useful in the methods of the invention. The diblock copolymer contains a homo-pNIPAAm block (n=130) for thermal responsiveness, a cationic DMAEAm-co-NIPAAm random copolymer block (m=15) to drive adsorption onto anionic AuNPs, and a terminal biotin moiety.

Polymer synthesis was carried out using two thermally-initiated RAFT polymerizations. The target molecular weight of the first RAFT polymerization was 15 kDa. A [NIPAAm]:[CTA]:[Initiator] ratio of 132:1:0.1 was used in p-dioxane. The homo-pNIPAAm product ((1) in FIG. 2) was purified and analyzed. GPC showed the polymer had M$_n$=15.7 kDa, polydispersity index (PDI)=1.01, and do/dc of 0.074. $^1$H NMR analysis confirmed the NIPAAm chemical shifts, with peaks at δ (ppm)=1.15 (s, R—CO—NH—CH—(CH$_3$)$_2$) and at δ (ppm)=4.00 (s, R—CO—NH—CH—(CH$_3$)$_{\overline{2}}$). These two peaks had an integrated peak area ratio of about 6:1, consistent with the proton ratio in the NIPAAm monomer.

Diblock extension was performed using the 15.7 kDa homo-pNIPAAm as a macro-chain transfer agent (mCTA). The mCTA was chain extended with a short random copolymer block of NIPAAm-co-DMAEAm. [NIPAAm]:[DMAEAm]:[mCTA]:[Initiator] ratios of 18:18:1:0.1 were used in MeOH. MeOH was chosen because the mCTA was highly soluble in MeOH. The diblock copolymer ((2) in FIG.

2) was found to have a $M_n$=17.7 by MALS, PDI=1.25, and dn/dc=0.071. $^1$H-NMR results from diblock copolymer preparations showed that the chemical shift of the DMAEAm methyl group protons was dependent on the protonation state of the tertiary amine. Diblock copolymers treated with 10 equivalents of NaOH to deprotonate the amines of DMAEAm were found to have DMAEAm methyl group shifts at δ (ppm) =2.26 (s, R—N(CH$_3$)$_2$. Polymers treated with 10 equivalents of HCl prior to NMR analysis, however, were found to have DMAEAm methyl group shifts at δ (ppm)=3.1 (s, R—N(CH$_3$)$_2$. The proton shift of the DMAEAm methyl group in monomeric form is δ (ppm)=2.26 (Chen, T. M., Wang, Y. F., Kitamura, M., Nakaya, T., and Sakurai, I. (1996) Synthesis and properties of poly(acrylamide)s containing both long chain alkyl groups and phosphatidylcholine analogues in the side chains. *Journal of Polymer Science Part a-Polymer Chemistry* 34, 1155-1164.). In analyzing the $^1$H-NMR, the four protons located between the amide and tertiary amine groups of DMAEAm were also assigned to the peak at δ (ppm)=3.1, which therefore represented 10 DMAEAm protons. The DPN of DMAEAm in the diblock was about 15, based on the 1:1.15 integrated peak area ratio of the single NIPAAm hydrogen at δ (ppm)=4.0 to the 10 DMAEAm protons at δ (ppm)=3.1. The overall NIPAAm:DMAEAm ratio in the diblock copolymer was about 9:1.

Biotinylation of Diblock Copolymer. NHS activation of the diblock copolymer was performed by dissolution of 1.29 g (73 μmol) of polymer, 76 mg (372 μmol) of DCC, and 42 mg (365 μmol) of NHS in 7 mL of DCM. The reaction proceeded for 24 hours at 22° C., at which time an additional 76 mg of DCC and 42 mg of NHS were added. The reaction was allowed to proceed for an additional 24 hours. The mixture was precipitated into pentane and dried under vacuum. The NHS-activated polymer was then mixed with 100 mg (266 μmol) of NH$_2$—PEG$_2$-biotin in 3 mL of DMF. The conjugation proceeded for 48 hours at 22° C. and was precipitated into diethyl ether. The product was dried under vacuum, dissolved in DI water, filtered through a 0.2 μm filter, and obtained through PD-10 column purification, and freeze-drying. Biotinylation efficiency was estimated using a commercially available HABA biotin quantification kit carried out according to manufacturer's instructions.

The 17.7 kDa diblock copolymer was biotinylated via DCC/NHS ester activation and conjugation to NH$_2$—PEG$_2$-biotin. The dicyclohexylurea byproduct was removed using a 0.2 μm syringe filter. Biotinylation efficiency was measured by commercially available HABA dye-displacement assay (Green, N. M. (1965) A spectrophotometric assay for avidin and biotin based on binding of dyes by avidin. *Biochemical Journal* 94, C23). Known amounts of polymer were added to a solution of HABA-saturated avidin. The decrease in absorbance at 500 nm due to HABA dye displacement from the binding pocket was measured. A standard curve generated by addition of variable amounts of free biotin to the HABA-saturated avidin was used as a reference to quantify the number of available biotin moieties in the polymer preparations. The biotinylation efficiency was found to be 78% for the 17.7 kDa diblock copolymer.

Nanoparticle Synthesis and Characterization. Citrate-stabilized colloidal gold was prepared according to the literature (Frens, G. (1973) Controlled nucleation for regulation of particle-size in monodisperse gold suspensions. *Nature-Physical Science* 241, 20-22). All glassware was cleaned with aqua regia, thoroughly rinsed with DI water, and dried in an oven before use. 150 mL of 0.1 mg/mL HAuCl$_4$ was brought to a boil in a round bottom flask. Sodium citrate, 1.76 mL of 10 mg/mL sodium citrate in DI, water was added. The reaction was boiled under reflux for 30 minutes and cooled to room temperature. The pH was raised to 8 by addition of 0.1 M NaOH. Next, 1.2 mL of a 10 mg/mL solution of 17.7 kDa biotinylated diblock copolymer in DI water was added. The flask was purged with N$_2$ for 45 minutes. The gold sol was then sealed and stirred at 22° C. for 24 hours in darkness, after which 1g of NaCl was added, followed by an additional 24 hours of stirring. The particles were then concentrated under 35 psi of N$_2$ using a membrane ultrafiltration system with a cellulose membrane (MWCO=100,000 kDa). The polymer-modified gold nanoparticles (AuNPs) were washed off of the membrane with 3 mL of PBS buffer. The AuNPs were stored in PBS at 4° C. under N$_2$ for up to 4 months and used for further streptavidin binding/enrichment studies.

Magnetic nanoparticles (mNPs) coated with 5 kDa homo-pNIPAAm (without biotin) were synthesized as previously described (Lai, J. J., Hoffman, J. M., Ebara, M., Hoffman, A. S., Estournes, C., Wattiaux, A., and Stayton, P. S. (2007) Dual magnetic-/temperature-responsive nanoparticles for microfluidic separations and assays. *Langmuir* 23, 7385-7391; Lai, J. J., Nelson, K. E., Nash, M. A., Hoffman, A. S., Yager, P., and Stayton, P. S. (2009) Dynamic bioprocessing and microfluidic transport control with smart magnetic nanoparticles in laminar-flow devices. *Lab on a Chip* 9, 1997-2002), with slight modification. Briefly, the 5 kDa homo-pNIPAAm was dissolved in tetraglyme (3.6 mM) at 100° C. Iron pentacarbonyl (Fe(CO)$_5$) was filtered through a 0.45 μm syringe filter prior to use. 4 μL Fe(CO)$_5$ per mL of tetraglyme was added. After 10 minutes of stirring, the temperature was raised to 180° C. for 5 hours. The reaction was cooled, and the mNPs obtained by precipitation into pentane, drying under vacuum, dialysis against DI water at 4° C., and freeze-drying. The mNPs were then dissolved in DI water at 50 mg/mL and stored at 4° C. for up to 3 months. TEM samples were prepared by dissolving particles in DI water (1 nM for the AuNPs, and 3 mg/mL for the mNPs). Particle solutions were aerosolized onto carbon-stabilized formvar-coated copper grids (Ted Pella) using a spray bottle.

Figure 3A:
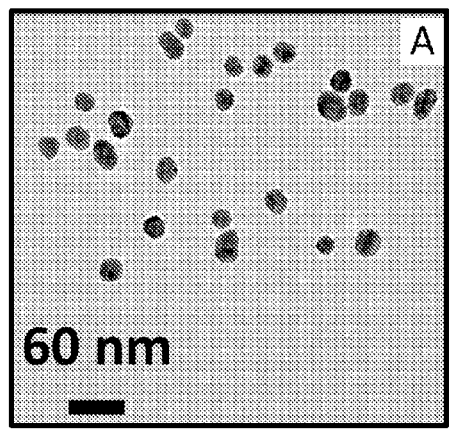
FIGS. 3A-3F provide characterization of representative magnetic (mNPs) and gold (AuNP) nanoparticles useful in the methods of the invention. TEM images, image analysis particle sizing histograms, and visible absorption spectra of AuNPs (FIGS. 3A-3C) and mNPs (FIGS. 3D-3F, respectively).
Figure 3B:
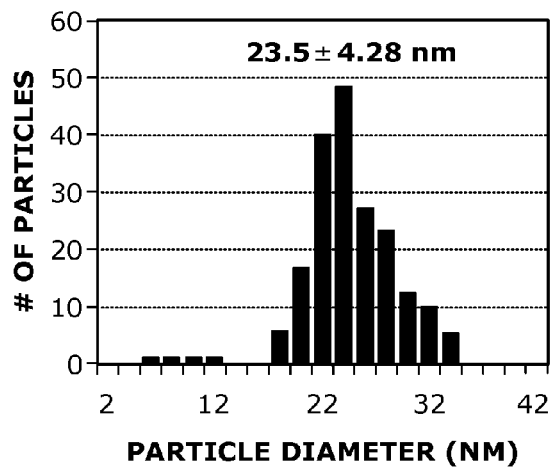
Figure 3C:
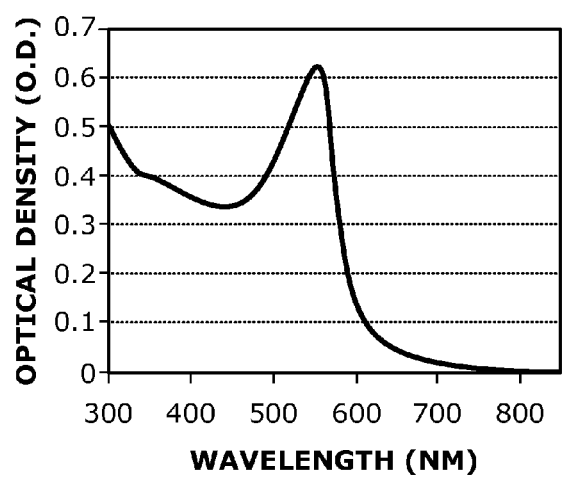

Citrate-stabilized gold nanoparticles were synthesized as noted above. Within 3 minutes of addition of sodium citrate to the boiling gold chloride solution, a rapid color change from yellow to deep red was observed. The positively charged diblock copolymer was allowed to interact with the negatively charged citrate-capped AuNPs overnight. In addition to electrostatics, chemisorption of the trithiocarbonate group from the RAFT CTA likely contributes to successful modification of the AuNPs. The polymer-modified AuNPs were then successfully transferred into 3 mL of 1×PBS buffer using membrane ultrafiltration. The AuNPs were washed off of the cellulose membrane and remained soluble for months stored in PBS buffer under N$_2$ at 4° C. AuNPs were characterized by TEM imaging, particle sizing image analysis, and absorption spectrophotometry (FIGS. 3A-3C). From TEM images, the AuNPs had pseudo-spherical morphology with diameter=23.5±4.28 nm (mean±standard deviation, # of particles counted>200). The LSPR absorption peak (FIG. 3C) was observed at 530 nm. The extinction coefficient of the 23 nm AuNPs was estimated to be $2*10^9$ M$^{-1}$cm$^{-1}$ from sizing data. This molar extinction coefficient was used in further studies to estimate the concentration of the AuNPs.

Figure 4A:
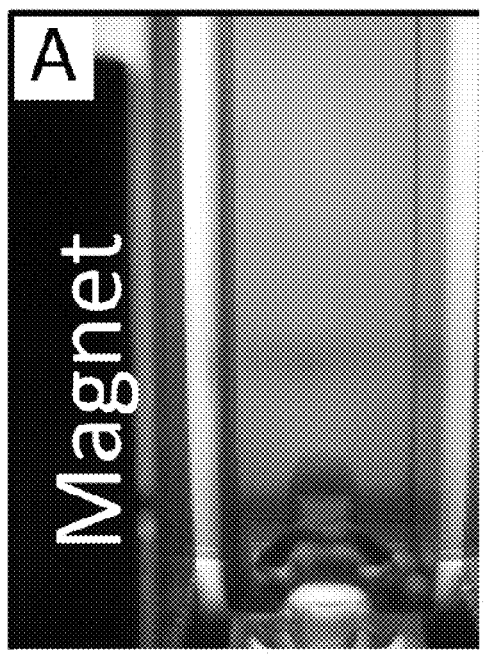
FIGS. 4A-4D are photographs of white light transmittance through nanoparticle solutions: mNPs below the polymer LCST (FIG. 4A) do not respond to the magnet, but above the LCST (FIG. 4B) are aggregated and magnetically pulled against the cuvette wall; AuNPs below the LCST (FIG. 4C) appear pink, while above the LCST (FIG. 4D) appear purple due to aggregation and near-field plasmonic coupling.
Figure 4B:
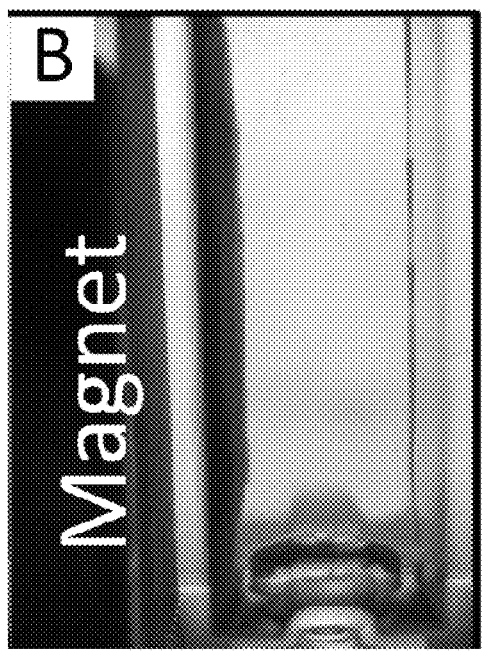
Figure 4C:
Figure 4D:
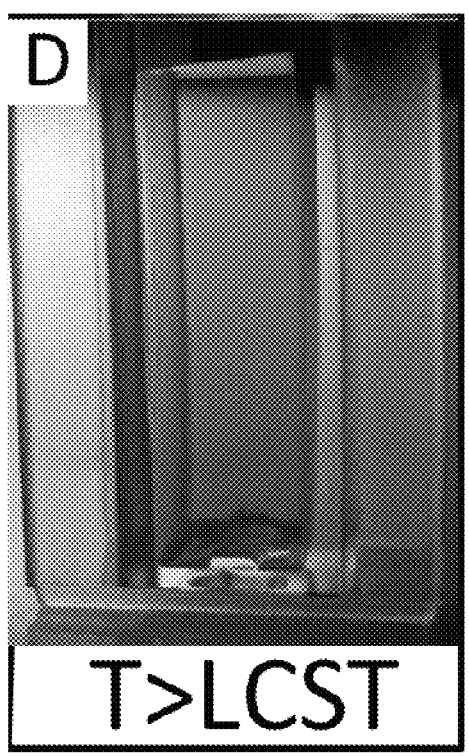
Figure 5A:
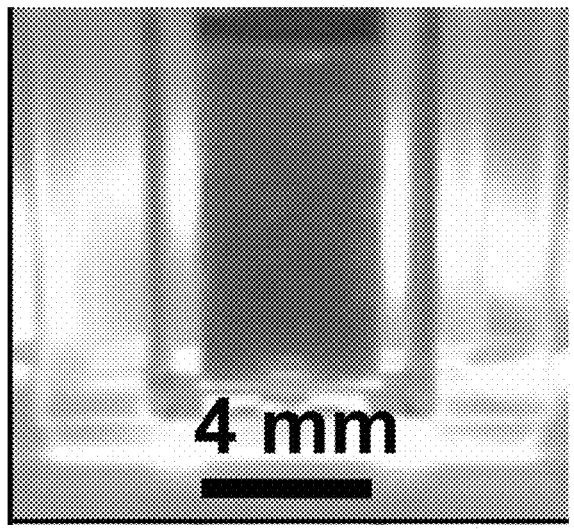
FIGS. 5A-5F are video still images of mixed AuNp/mNP co-aggregation and magnetic separation in accordance with a representative method of the invention. The sample comprises 250 µL of AuNP/mNP/homo-pNIPAAm mixtures in PBS buffer. 250 µL of 5M NaCl was used to trigger the pNIPAAm phase transition (ion strength-responsive polymer transition) seconds before the image in FIG. 5A was acquired. The magnet was applied for a total of 20 minutes and images were recorded. Comparable magnetic separation behavior was observed for mixtures that were co-aggregated using a thermal stimulus. The AuNP particle capture efficiency was evaluated by measuring the absorbance at 530 nm before and after magnetic capture and re-suspension into an equal volume of fluid below LCST. Typical nanoparticle capture efficiencies from 50% human plasma were found to be 75-85%.
Figure 5B:
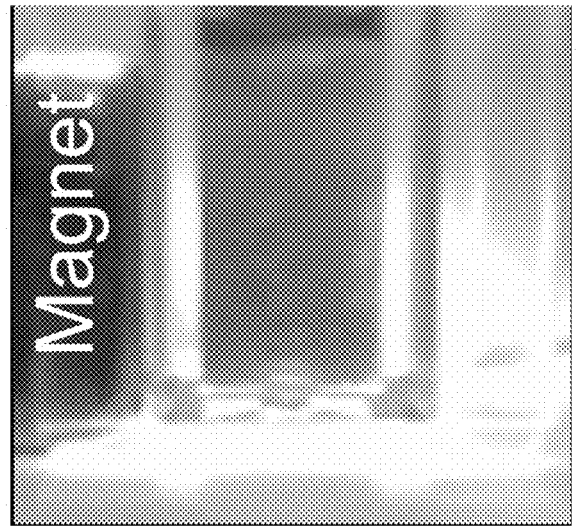
Figure 5C:
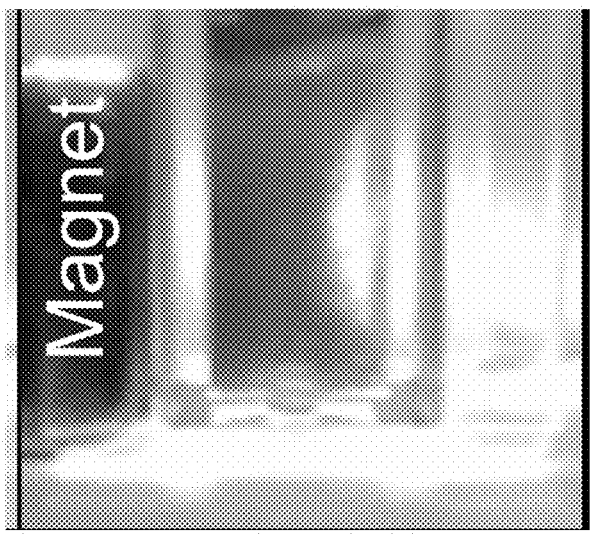
Figure 5D:
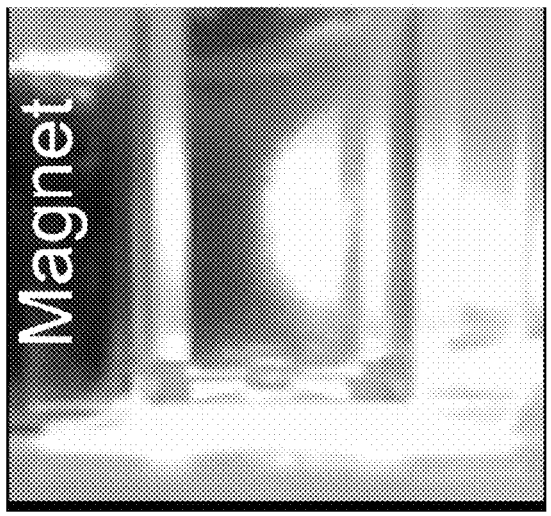
Figure 5E:
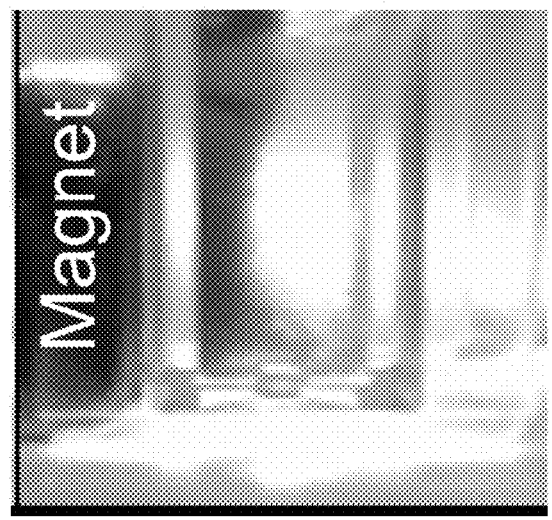
Figure 5F:
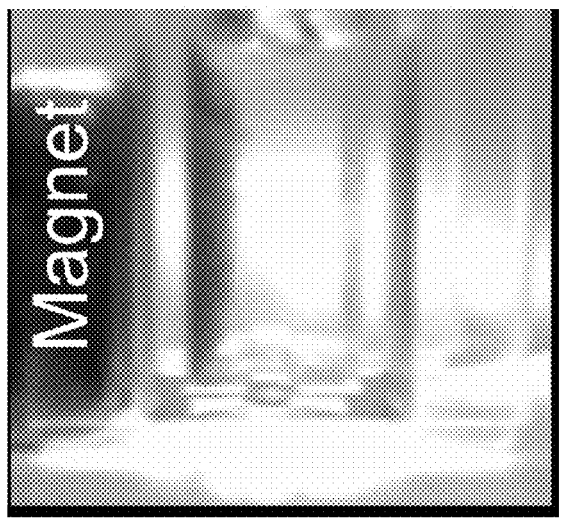

Unlike citrate-stabilized AuNPs, the polymer-modified AuNPs were found to be colloidally stable in physiological buffers (e.g., PBS). The localized surface plasmon resonance (LSPR) wavelength did not red-shift after transfer of the particles into PBS buffer. The LSPR wavelength of the AuNPs was red-shifted upon raising the temperature above the LCST of the polymer (FIGS. 4C and 4D). Below the LCST, the gold colloid had an absorption peak at 530 nm, and transmitted white light appears pink (FIG. 4C). After raising the temperature above the LCST, the LSPR was red-shifted by about 40 nm and the solution appeared purple (FIG. 4D). The color change is due to dielectric coupling of LSPR oscillations between aggregated AuNPs in close proximity to each other. The red-shift of the LSPR was prevented upon addition of 0.2 mg/mL of homo-pNIPAAm free polymer. Addition of free polymer insulates the AuNPs from one another, preventing them from becoming sufficiently close in proximity to allow for coupling of the LSPR.

Figure 3D:
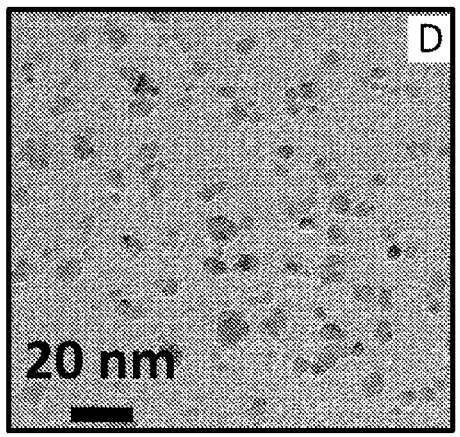
Figure 3E:
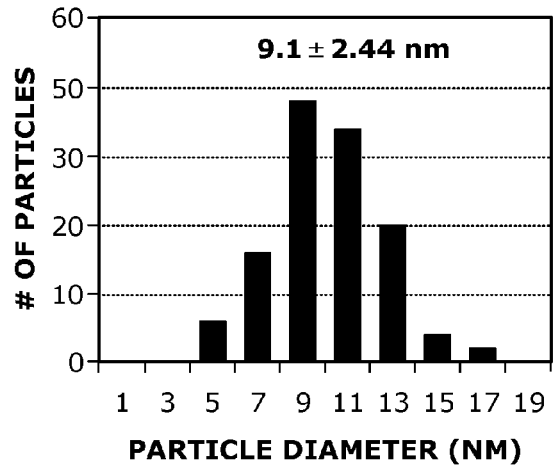
Figure 3F:
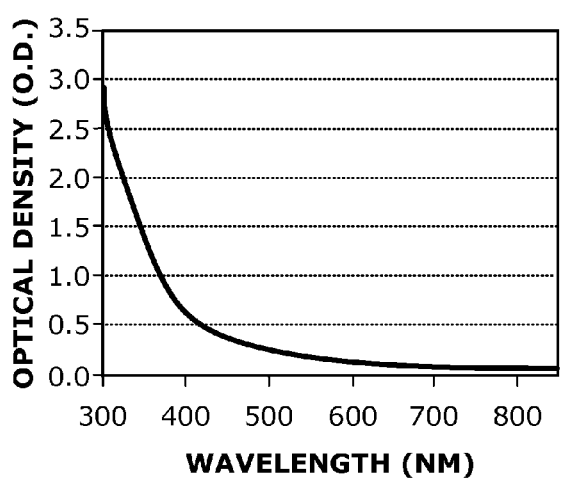

The mNPs were synthesized using a 5-kDa homo-pNIPAAm, as noted above. This homo-pNIPAAm served as a stabilizer during mNP synthesis, resulting in pNIPAAm-coated mNPs. TEM and particle size analysis of the mNPs (FIGS. 3D and 3E) showed they have an average long-axis diameter of 9.1±2.44 nm (mean±standard deviation, # of particle counted>60). The optical absorption spectrum of the mNPs shows a Rayleigh scattering profile, as seen in FIG. 3F. The mNPs exhibit a thermally triggered increase in the magnetophoretic mobility. This behavior is demonstrated in FIGS. 4A-4D: below the LCST (FIG. 4A), the mNPs do not rapidly respond to the magnet placed against the side of the cuvette because they exist as the <10 nm particles. When the temperature is raised above the polymer LCST (FIG. 4B), the large aggregates have much larger magnetophoretic mobility, and are rapidly separated against the cuvette side-wall by the magnet.

Both particle types (AuNPs and mNPs) therefore exhibit thermally-triggered aggregation that modulates their magnetic and/or optical properties. It was found that mixtures of these two particle types possessed both the magnetic separation behavior of the mNPs combined with the optical extinction properties of the AuNPs. AuNPs modified with the diblock copolymers could therefore be magnetically separated upon co-aggregation with the pNIPAAm-coated mNPs and application of a magnetic field gradient. Video stills demonstrating magnetic separation of AuNPs are provided in FIGS. 5A-5F.

Magnetic Enrichment of ALEXAFLUOR-750-Labeled Streptavidin. Pooled human plasma was diluted with an equal volume of 2×PBS (20 mM phosphate, 276 mM NaCl, 5.4 mM KCl, pH 8.0). ALEXAFLUOR-750-labeled streptavidin (AF-750 streptavidin) was spiked into the 50% human plasma at a concentration of 5 nM. Stock solutions of the nanoparticle reagents were added to achieve final concentrations of 3 nM and 2 mg/mL for the AuNPs and mNPs, respectively. 8 kDa Homo-pNIPAAm free polymer was added to a final concentration of 2 mg/mL. As a negative control, 1 µM free biotin was included in the plasma dilution buffer. AF-750 streptavidin, 100, 250, or 500 µL of the 5 nM AF-750 streptavidin in 50% human plasma, was added to Eppendorf tubes. Samples were incubated for 15 minutes with orbital shaking (400 rpm) inside an aluminum tube-holder equilibrated in an incubator set to 45° C. This was followed by incubation of the sample tubes in close contact with neodymium iron boron magnets for 15 minutes at 45° C. using an in-house fabricated magnet holder. Next, the supernatant was discarded with a pipette, and the precipitate that had been captured along the side of the tube was re-suspended into 10 µL of 1×PBS pH 6.0 buffer at 4° C. Fluorescence of the AF-750 streptavidin ($\lambda_{ex}$=752 nm, $\lambda_{em}$=776 nm), and absorbance of the AuNPs at 520 nm were measured using a fluorescence/absorbance microwell plate reader (Tecan).

As a validation of the bioseparation technique, the ability of AuNPs to bind fluorescently labeled streptavidin, and concentrate the target protein via polymer-induced co-aggregation and magnetic separation with mNPs was tested. An advantage of this nanoparticle system is the ability to process large sample volumes as easily as µL quantities. This capability was demonstrated by increasing the total processed sample volume at a fixed concentration of labeled streptavidin. AF-750 streptavidin (5 nM) spiked into 50% human plasma was used to mimic a clinical sample. 3 nM of diblock-copolymer-modified AuNPs, 2 mg/mL mNPs, and 2 mg/mL of 8 kDa homo-pNPAAm were added sequentially. Each AuNP is expected to bind no more than 50 streptavidin molecules based on nanoparticle size and a theoretical streptavidin monolayer density of 2.8 ng/mm$^2$.

Figure 6:
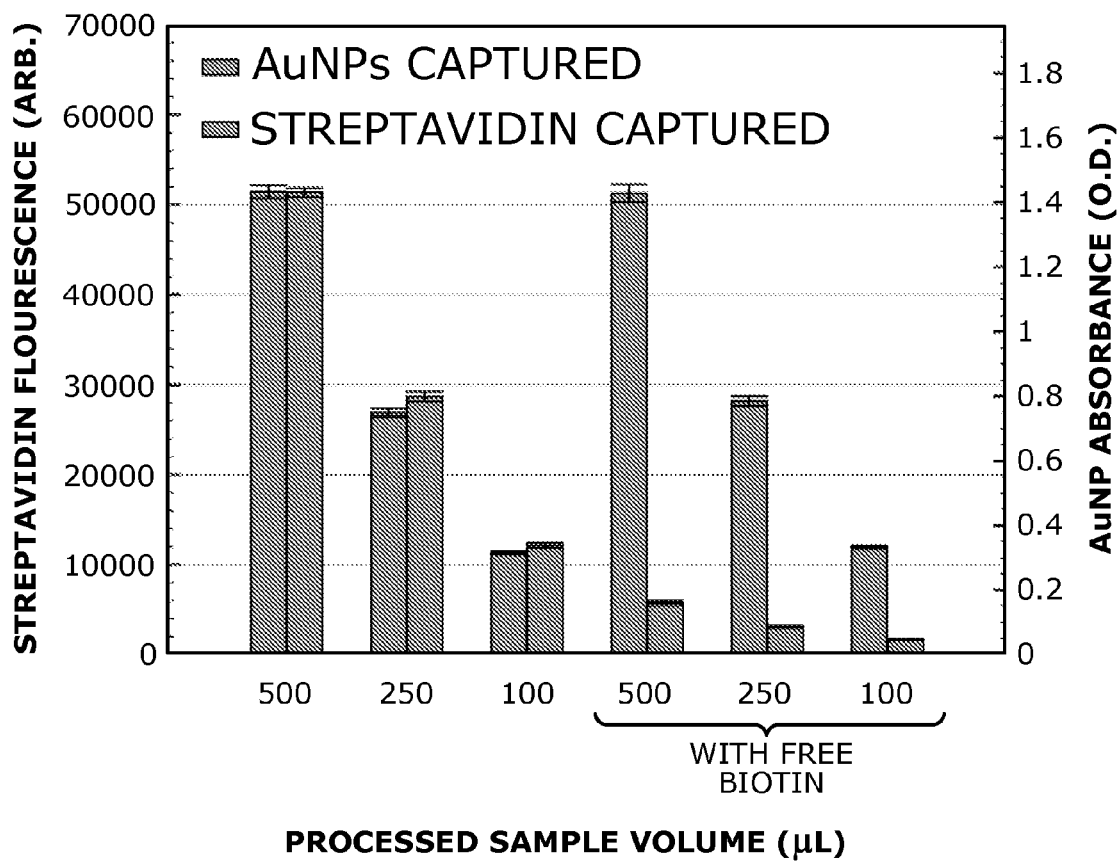
FIG. 6 is a graph demonstrating magnetic enrichment of fluorescent-streptavidin by AuNP/mNP mixtures. AF-750 labeled-streptavidin fluorescence and AuNP absorbance were measured after processing variable volumes of 50% human plasma containing 5 nM fluorescent-streptavidin. In all cases, the captured particles were redissolved into 10 µL of PBS 6.0 buffer, achieving a 50-fold, 25-fold, or 10-fold particle/protein enrichment factor for the 500, 250, and 100 µL samples, respectively. Samples spiked with 1 µM free biotin served as negative controls to block the streptavidin binding sites preventing fluorescence capture, while particle capture/absorbance remained high.

Samples of 100, 250, or 500 µL were heated to 45° C. causing polymer collapse and mixed AuNP/mNP aggregate self-assembly. A magnet was applied, and the aggregates were captured at the side of the carrying vessel. The supernatant was discarded, and the captured pellet was re-dissolved into a 10 µL volume of cool (<LCST) PBS 6.0 buffer. FIG. 6 shows fluorescence and absorbance measurements taken on the re-dissolved aggregates below the LCST. Data bars in FIG. 6 represent mean±SD (n=5) of labeled-streptavidin fluorescent intensity at 776 nm, or particle absorbance at 520 nm. Increasing the sample volume results in a corresponding linear increase in the AuNP absorbance and streptavidin fluorescence. In the presence of free biotin, the streptavidin binding sites are blocked and fluorescence capture is eliminated, demonstrating that capture is occurring via specific streptavidin-biotin binding. Only a small amount of fluorescence is captured due to non-specific adsorption of the labeled-streptavidin to the nanoparticle/polymer aggregates.

LFIA Device Fabrication. Rabbit polyclonal anti-streptavidin IgG was deposited at 3 mg/mL onto HiFlow 180 nitrocellulose assay membranes using an in-house fabricated protein striping system. The membrane was diced into rectangles measuring 16×3 mm using a $CO_2$ laser system (Universal Laser Systems). The strips were submerged in goat protein non-specific blocking solution (Zymed) for 30 minutes, followed by drying in a vacuum desiccator overnight. The strips were then applied to adhesive coated mylar substrates measuring 48×3 mm. An absorbent pad (35×3 mm) was placed at the distal end of the flow strip to drive capillary wicking of the fluids. The length of the overlap between the assay membrane and the absorbent pads was 3 mm. LFIA strips were stored in a desiccator at 23° C. and used within one week.

Figure 7A:
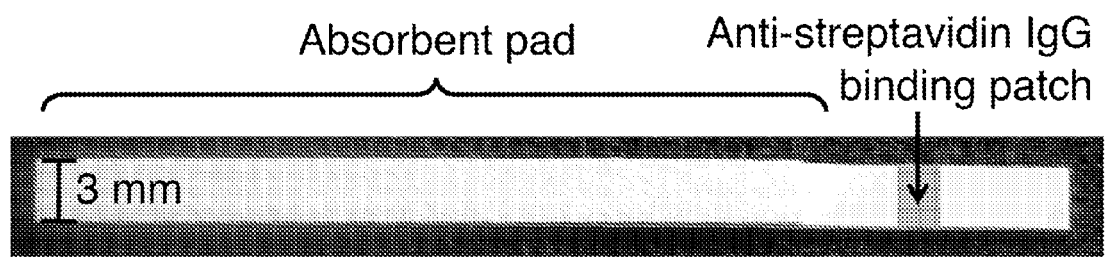
FIGS. 7A and 7B relate to a lateral flow immunoassay in accordance with a representative method of the invention.

The capabilities of the bioseparation/enrichment system were demonstrated by developing a quantitative lateral flow immunoassay of the model protein analyte streptavidin. LFIA strips were fabricated using and in-house protein striping system capable of depositing the capture antibody (rabbit polyclonal anti-streptavidin IgG) within the confines of a narrow line about 1.5 mm in width onto nitrocellulose substrates. The nitrocellulose strips and absorbent wicking pads were placed onto adhesive-coated mylar. An image of the lateral flow strip is shown in FIG. 7A.

Effect of Streptavidin Dose on LFIA Signal. 200 µL Samples of 50% human plasma containing variable amounts of non-fluorescent streptavidin, from 50 ng/mL to 0 ng/mL, were prepared. The AuNPs, mNPs, and 8 kDa homo-pNIPAAm were added to achieve final concentrations of 3 nM, 2 mg/mL, and 2 mg/mL, respectively. Heating, magnetic separation, and removal of the supernatant were performed as described in the fluorescent capture study (see above). The magnetically captured particle aggregates were resuspended into 10 µL of 1×PBS pH 6.0 at 4° C. 10 µL Droplets of the captured protein/particle mixture were deposited into wells of a 96-well plate. LFIA strips were placed into the droplets, which completely wicked into the strips within 5-6 minutes.

The membranes were then transferred to wells containing PBS pH 6.0 rinse buffer. The buffer rinse was allowed to proceed for 20 minutes, or until the absorbent pad was saturated. Imaging of the developed strips was performed using a digital camera (Canon SD400) on digital macro setting. Strips were illuminated from behind at an oblique angle using a white light source, and the transmission images were quantified by image analysis. All samples were run in triplicate on three separate LFIA strips, and imaged under identical lighting conditions.

Image analysis was performed using Image J software. The background-corrected mean pixel intensity of the green channel in the RGB images was measured from a region of interest encompassing the leading edge of the antibody binding patch.

Figure 7B:
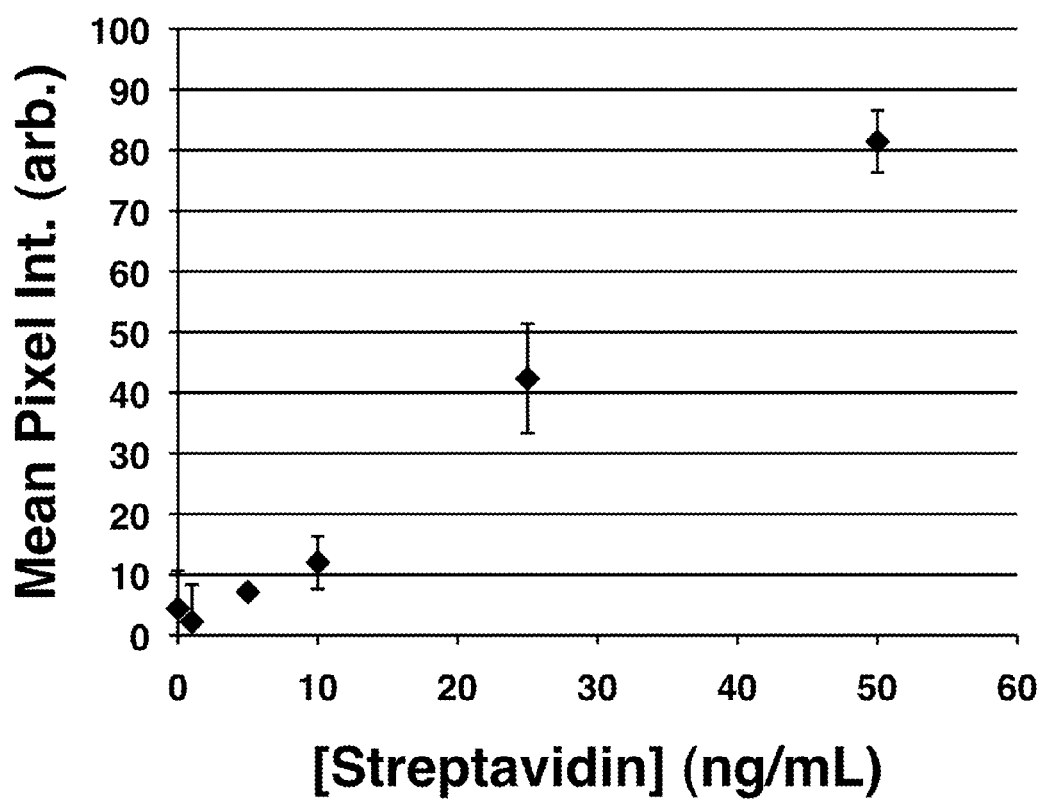

FIG. 7B shows the light extinction signal generated by processing varying amounts of streptavidin from 200 μL sample volumes, and flowing the re-suspended particle mixtures through the capture antibody line on the LFIA strips, followed by a rinse step. The curve is linear with a limit of detection of 6 ng/mL, determined using 3 times the standard error of the zero antigen sample as the lower signal limit. The dual AuNP/mNP nanoparticle system is therefore able to generate specific signal proportional to the amount of diagnostic target in the sample, facilitating quantitative assays when combined with optical reader technologies.

Effect of Increasing Sample Volume on LFIA Signal. 10 ng/mL Streptavidin in 50% human plasma was prepared. Stock solutions of the nanoparticle/polymer reagents were added to achieve final concentrations of 3 nM, 2 mg/mL, and 2 mg/mL for the AuNPs, mNPs, and 8 kDa homo-pNIPAAm free polymer, respectively. The stock protein/particle solution at a fixed streptavidin concentration (10 ng/mL) was divided into aliquots of 100, 200, 300, 400, or 500 μL. Each sample tube was processed as described above. The captured aggregates were resuspended into 10 μL of 1×PBS pH 6.0 buffer at 4° C. 10 μL Droplets of the concentrated particle mixture were run on the LFIA strips following the protocol described for the dose-response experiment (see above).

Figure 8:
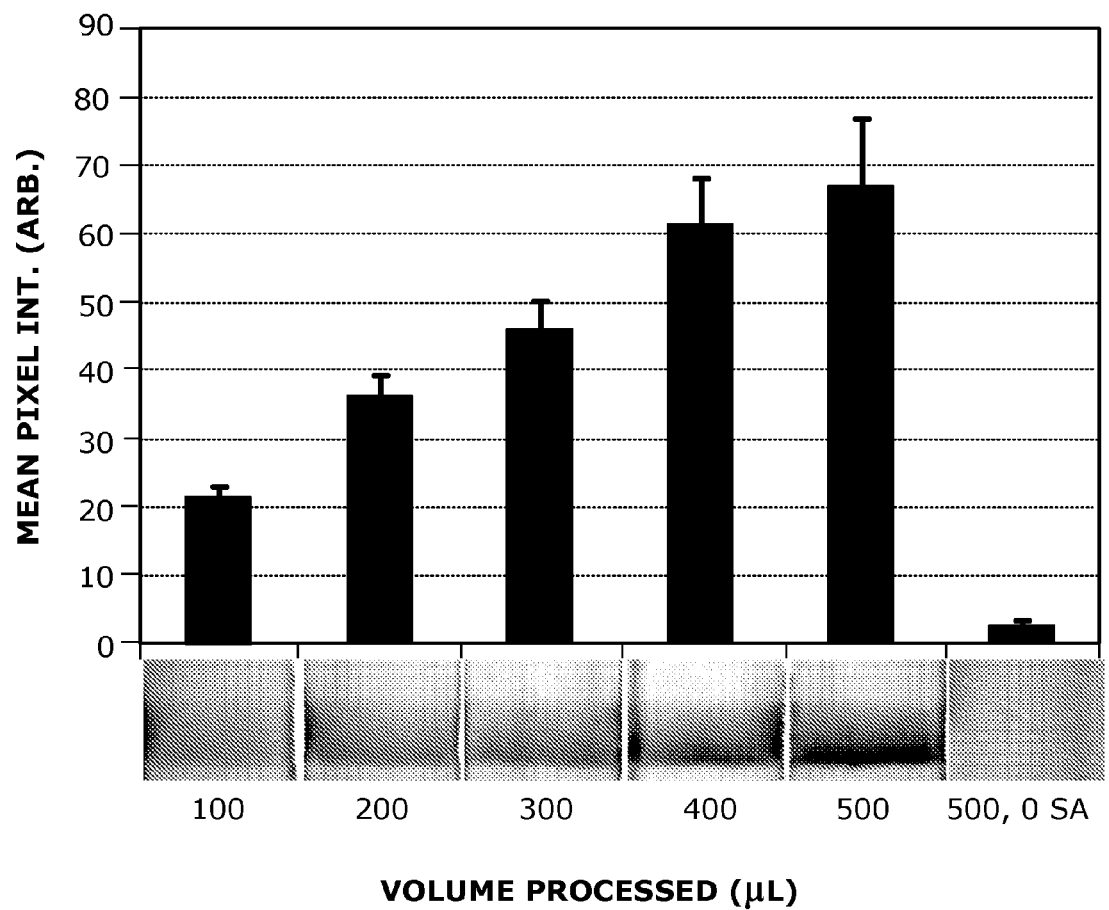
FIG. 8 illustrates the effect of increasing sample volume on LFIA signal. Increasing sample volumes from 100-500 µL each with the same concentration of streptavidin (10 ng/mL)

Effect of Concentrating Model Biomarker from a Larger Sample Volume on LFIA Signal. Increasing the volume of the sample processed at a fixed concentration of streptavidin effectively captured more molecules of the target protein, which translates into increased light extinction at the test line of the LFIA strip. FIG. 8 shows the increase in LFIA signal that was accomplished by increasing the sample volumes from 100-500 μL for a fixed 10 ng/mL of streptavidin. A 500 μL sample without streptavidin (500, 0 SA) served as the negative control. These results demonstrate that the smart nanoparticle system can increase the signal at a fixed analyte concentration by processing larger volumes of sample. Where larger samples can be obtained from the patient, this finding has implications for opening up new biomarkers to point-of-care testing that are currently too dilute to be detected by conventional non-concentrating LFIA.

Example 2

Preparation and Characterization of Representative Magnetic and Non-Magnetic Particles and Their Use in a Representative Multiplexed Method of the Invention In this example, the preparation and characterization of representative magnetic and non-magnetic particles useful in the methods of the invention are described. The use of these particles in a representative multiplexed method of the invention is also described.

FIG. 9 is a schematic illustration of a representative non-magnetic particle useful in the practice of the methods of the invention for capturing a biomarker. This universal bioconjugate design allowed for facile multiplexing by simply adding multiple different biotinylated antibodies to the sample before addition of the universal streptavidin-gold reagent. FIG. 10 is a schematic representation of a representative method of the invention, a magnetic enrichment lateral flow immunoassay, utilizing the universal streptavidin-gold reagent.

Polymer Synthesis. Reversible addition fragmentation chain transfer (RAFT) polymerization was carried out using previously published procedures (Lai, J. J. et al. Dual magnetic-/temperature-responsive nanoparticles for microfluidic separations and assays. Langmuir 23, 7385-7391 (2007); Nash, M. A., Lai, J. J., Hoffman, A. S., Yager, P. & Stayton, P. S. "Smart" Diblock Copolymers as Templates for Magnetic-Core Gold-Shell Nanoparticle Synthesis. Nano Letters 10, 85-91, doi:10.1021/n1902865v (2010)). Briefly, a homo-pNIPAAm polymer with a target molecular weight of 15 kDa was polymerized in a round bottom flask. 3.11 Grams (27.5 mmol) of NIPAAm, 85 mg (0.212 mmol) of DCT, and 3.4 mg (20.8 μmol) of AIBN were mixed in 6 grams of p-dioxane. The oxygen was removed by purging with nitrogen for 30 minutes, followed by incubation at 60° C. for 18 hours. The macro chain transfer agent (mCTA) product was obtained by precipitation into pentane, drying under vacuum, dialysis against DI water at 4° C., and freeze-drying. Diblock chain extension was accomplished by dissolving in a round-bottom flask 2g (117 μmol) of a 17.1 kDa homo-pNIPAm mCTA, 0.3 g (2.1 mmol) of DMAEAm, 0.2325 g (2.05 mmol) of NIPAAm, and 1.9 mg (11.6 μmol) of AIBN in 8 mL of MeOH. This resulted in a [DMAEAm]:[NIPAAm]:[mCTA]:[initiator] ratio of 18:18:1:0.1. The flask was purged with nitrogen and heated to 60° C. for 18 hours. The MeOH solvent was then removed by rotary evaporation, and the product dissolved in 5 mL of THF, and precipitated into pentane. The precipitate was dried under vacuum, dissolved in 15 mL of DI water, purified by PD-10 desalting column (GE Healthcare), and freeze-dried. The lyophilized powder was dissolved at 10 mg/mL in DI water and further used for surface modification of AuNPs.

The polymer incorporates a thermally-responsive pNIPAAm block, and a pH-responsive p(NIPAAm-co-DMAEAm) cationic random copolymer block to drive polymer adsorption onto negatively charged citrate-stabilized AuNPs.

Polymer Analysis. Polymers were characterized using size exclusion chromatography performed on an Agilent 1200 series liquid chromatography system, equipped with TSKgel alpha 3000 and TSKgel alpha 4000 columns (TOSOH biosciences). The mobile phase was LiBr (0.01 M) in HPLC grade DMF at a flow rate of 1 mL/min. Multi-angle light scattering data were obtained on a miniDAWN TREOS (Wyatt Technologies Corp.) with a 658 nm laser source, and three detectors at 45.8°, 90.0°, and 134.2°. The instrument calibration constant was 4.7460*10-5 V-1cm-1. The refractive index was measured using an Optilab Rex detector (Wyatt Technologies Corp.). The dn/dc value for the homo-pNIPAAm mCTA was determined under the assumption of 100% mass recovery. The dn/dc value for the diblock copolymer was determined by injecting polymer samples at known concentrations into the RI detector post-column. The diblock dn/dc value was then calculated using linear regression with the Astra 5.3.4.14 data analysis software package (Wyatt Technologies Corp.). $^1$H-NMR (300 MHz) spectroscopy in $CDCl_3$ was performed on a Bruker AV300. Gold nanoparticle absorption was measured on a Hewlett Packard 8453 diode array extinction spectrophotometer with a temperature-controlled quartz cuvette sample holder.

Size exclusion chromatography with multi-angle light scattering detection showed the homo-pNIPAAm polymer had a molecular weight Mn=17.1 kDa, with a polydispersity index PDI=1.04, and dn/dc of 0.076. Diblock chain extension with a random copolymer of NIPAAm and DMAEAm was performed using the 17.1 kDa homo-pNIPAAm polymer as a macro chain transfer agent in methanol. Size exclusion chromatography showed that the diblock copolymer had Mn=21.5 kDa, PDI=1.11, and dn/dc of 0.071. $^1$H-NMR performed in $CDCl_3$ confirmed the chemical composition and showed that the chemical shifts of the DMAEAm protons were dependent on the protonation state of the tertiary amine groups in the polymer. The overall composition of the diblock copolymer was about 12% DMAEAm and about 88% NIPAAm. The ionizable DMAEAm amine groups in the second block caused the diblock copolymer to have a pH-dependent thermal aggregation profile as shown in FIG. 11. At pH 6 and 7, the DMAEAm amine groups are protonated and very little light scattering is observed when the sample is heated above the LCST. However, at pH 8, more of the amine groups are uncharged and the polymer exhibits a slightly lower LCST, and forms larger aggregates that scatter more light as compared to pH 6 or 7.

Magnetic Nanoparticle Synthesis. Magnetic nanoparticles (mNPs) with a 5 kDa homo-pNIPAAm corona were synthesized as previously described (Lai, J. J. et al. Dual magnetic-/temperature-responsive nanoparticles for microfluidic separations and assays. Langmuir 23, 7385-7391 (2007); Lai, J. J. et al. Dynamic bioprocessing and microfluidic transport control with smart magnetic nanoparticles in laminar-flow devices. Lab on a Chip 9, 1997-2002, doi:10.1039/b817754f (2009)). Briefly, the 5 kDa homo-pNIPAAm was dissolved in tetraglyme (3.6 mM) at 100° C. Iron pentacarbonyl (Fe(CO)$_5$) was filtered through a 0.45 µm syringe filter prior to use. 4 µL Fe(CO)$_5$ per mL of tetraglyme was added. The temperature was then raised to 180° C. for 5 hours. The reaction was cooled, and the mNPs obtained by precipitation into pentane, drying under vacuum, dialysis against DI water at 4° C., and freeze-drying. The mNPs were dissolved in DI water at 50 mg/mL and stored at 4° C. for up to 3 months prior to use.

Gold Nanoparticle Synthesis. Citrate-stabilized colloidal gold was prepared according to the literature (Frens, G. Controlled nucleation for regulation of particle-size in monodisperse gold suspensions. Nature-Physical Science 241, 20-22 (1973). All glassware was cleaned with aqua regia, thoroughly rinsed with DI water, and dried before use. 150 mL of 0.1 mg/mL HAuC14 was brought to a boil in a round bottom flask. 1.76 mL of 10 mg/mL sodium citrate in DI water was rapidly added. The reaction was refluxed for 30 minutes and cooled to room temperature. The pH was raised to 8.2 by addition of 0.1 M NaOH. Next, 1.2 mL of a 10 mg/mL solution of 21.5 kDa diblock copolymer in DI water was added. The flask was purged with N2 for 45 minutes, and stirred at 22° C. for 24 hours in darkness. Next, 1g of NaCl was added, followed by an additional 24 hours of stirring. The particles were then concentrated under 35-40 psi of nitrogen in a membrane ultrafiltration system with a cellulose membrane from Millipore (regenerated cellulose, 44.5 mm diameter, NMWL 100,000, product #14422AM). The polymer-modified AuNPs were washed off the membrane with 2 mL of 0.1 M MES buffered saline at pH 5.0. The AuNPs in MES buffer were used for NHS-ester activation and conjugation to streptavidin within 24 hours.

Negatively charged gold nanoparticles were synthesized using trisodium citrate as a reducing agent and stabilizing ligand. The AuNPs had pseudospherical morphology observed by TEM with diameters of about 20 nm. TEM of the AuNPs and mNPs are shown in FIGS. 12 and 13, respectively. After boiling for 30 minutes, the reaction mixture was cooled and the pH was raised to 8.2, near the pKa of the DMAEAm monomer. The diblock copolymer in DI water was then added and adsorbed onto the gold colloid overnight. After 24 hours, 1g of NaCl was added to shield electrostatic interactions, and no particle flocculation occurred indicating successful particle stabilization. Incorporating a cationic polymer segment greatly facilitated AuNP colloidal stability in physiological buffers, and prevented salt-induced particle flocculation better than trithiocarbonate or secondary thiol terminated homo-pNIPAAm polymers of equivalent molecular weight. These observations are supportive of electrostatic interactions being the primary means of interaction between the AuNPs and the polymers.

The diblock copolymer-modified AuNPs exhibit a thermally triggered red shift of the localized surface plasmon resonance (LSPR) resulting from plasmonic coupling between aggregated particles. The extent of the LSPR red shift can be used as a nanoscopic ruler by which nanoscale interactions between the particles determine the macroscopic absorption behavior of the solution. The pH-dependent aggregation profile exhibited by the polymer was conferred to the polymer-modified AuNPs. The red shift of the LSPR shows a pH-dependent aggregation profile consistent with that of the polymer. The room temperature LSPR at 532 nm upon heating the AuNP solution above the LCST in PBS buffer at pH 8 was red shifted by about 133 nm to $\lambda$=665 nm. At pH 6, however, the LSPR was only shifted by about 78 nm to $\lambda$=610 nm, suggesting that protonation of the polymeric amines electrostatically inhibits close aggregation and plasmonic coupling. These data are shown in FIG. 14.

Conjugation of Gold Nanoparticles to Streptavidin. Two mL of the diblock copolymer-modified AuNPs (about 70 nM in MES buffered saline at pH 5.0) were mixed with 13.1 mg of Sulfo-NHS and 14.8 mg of EDC in dry form. The NHS-ester activation proceeded for 40 minutes at room temperature with orbital shaking. Buffer exchange was then performed with a centrifugal size exclusion column (Zeba desalting spin column, Pierce) to transfer the AuNPs to 1×PBS 7.3 buffer. The NHS-activated AuNPs were then added to lyophilized wild type streptavidin protein (U.S Biological, Swampscott, Mass.), and allowed to react overnight at room temperature with orbital shaking. After conjugation to streptavidin, the reaction volume was increased to 50 mL with 1×PBS 7.3 buffer. The 50 mL volume was concentrated using membrane ultrafiltration as described above. This dilution/enrichment process was repeated two more times while the absorbance of the membrane eluent was monitored at 280 nm to confirm the removal of non-conjugated streptavidin. The final product (SA-AuNPs) was rinsed off the membrane with PBS buffer, pH 7.3. The SA-AuNPs were stored (about 80 nM) in PBS at 4° C. under nitrogen for up to 3 months and used for further immunoassay studies.

After successful modification of the AuNPs with the polymer, the semi-telechelic carboxyl group on the polymer was conjugated to lysine amine groups on streptavidin using carbodiimide chemistry, forming the product SA-AuNPs. Membrane ultrafiltration was used to remove non-conjugated streptavidin from the reaction mixture. This purification process was monitored by measuring the 280 nm UV absorbance of streptavidin in the buffer that was removed during membrane ultrafiltration. As shown in FIG. 15, after three rounds of ultrafiltration, no streptavidin absorbance at 280 nm was measured from the filtered particle eluent, indicating that the non-conjugated streptavidin had been removed. Confirmation of streptavidin conjugation to the gold particles was confirmed using an immunochromatographic flow strip. The SA-AuNPs were flowed through a small (3 mm×30 mm) piece of nitrocellulose that had been modified with a stripe of anti-streptavidin IgG (Abcam, product #AB6676). As the SA-AuNPs flowed through the capture zone, the accumulation of red color at the location of IgG surface modification was used to confirm streptavidin modification of the gold reagent.

The thermally triggered red shift of the LSPR was monitored by heating the SA-AuNP reagent from room temperature to 45° C. in 15 minutes at pH 6, 7, or 8. After conjugation to streptavidin, the room temperature AuNP resonance at $\lambda=532$ nm at pH 8 was red shifted by 58 nm to $\lambda=590$ nm, while at pH 6 was only red shifted by 38 nm to $\lambda=570$ nm. These results are shown in FIG. 16. When compared with the identical experiment performed with non-conjugated AuNPs, these results are consistent with the 55 kDa streptavidin protein limiting the extent to which the AuNPs could undergo plasmonic coupling, resulting in a less severely red shifted LSPR. The increased hydrophilic protein mass attached to the polymeric corona sterically inhibited close particle-particle plasmonic coupling and tended to depress the LSPR red shift.

Biotinylation of anti-PfHRP2 IgG and anti-aldolase IgG Antibodies. Monoclonal mouse anti-PfHRP2 IgG (product #MPFG-55A), and monoclonal mouse anti-aldolase IgG (product #RPVA-55A) were purchased from Immunology Consultants Laboratory (Newberg, Oreg.). Modification of the IgG antibodies was performed using an NHS-activated biotin containing a chromophore linker. The NHS-chromogenic-biotin (Pierce, Rockford, Ill.) dissolved at 10 mg/mL in anhydrous dimethylformamide was added in a 7.5 molar excess to the IgG protein at 1 mg/mL in PBS buffer, pH 7.3 at room temperature. After 3-hours the unreacted NHS-chromogenic-biotin was removed using a centrifugal size-exclusion column (Zeba desalting column, Pierce). The degree of biotinylation was estimated by measuring the ratio of the biotin-chromophore extinction ($\epsilon=29,000$ $M^{-1}cm^{-1}$ at 354 nm) to the IgG extinction ($\epsilon=186,000$ $M^{-1}cm^{-1}$ at 280 nm).

A commercial NHS-chromogenic-biotin was conjugated to lysine amine groups on the IgG antibodies. After conjugation and purification, the ratio of chromophore linker absorbance at 354 nm was compared with IgG absorbance at 280 nm to estimate the degree of biotinylation. For the anti-PfHRP2 IgG, a 1:20 dilution of the antibody solution showed A280/A354=0.116/0.068. Given the biotin-chromophore extinction coefficient ($\epsilon=29,000$ $M^{-1}cm^{-1}$ at 354 nm), and the IgG extinction coefficient ($\epsilon=186,000$ $M^{-1}cm^{-1}$ at 280 nm), the measured absorbance ratio corresponds to 3-4 biotins per IgG. The degree of biotinylation of the anti-aldolase IgG used in the multiplexed assay was measured to be about 1-2 biotins per IgG using the same method.

Lateral Flow Device Modification. Commercial immunochromatography devices with a control line of anti-mouse antibody, and two test lines of anti-aldolase and anti-PfHRP2 antibodies were purchased from Sanitoets/Sallamander Concepts CC (Lynnwood Pretoria, South Africa). The commercial flow strips were removed from the plastic cassette, and the dried gold-conjugate pad was carefully removed and discarded. The backing of the strip was cut just upstream of the patterned nitrocellulose assay membrane. The strip was then re-mounted onto a strip of adhesive-coated mylar (4 mm wide×38 mm long). A porous rectangular sheet of cellulose fiber (4×5×0.42 mm, grade #8301, Ahlstrom, Mount Holly Springs, Pa.) was placed on the nitrocellulose membrane upstream of the capture lines in order to serve as an aggregate filter and liquid reservoir for the nanoparticle mixtures while the sample liquid was imbibed into the nitrocellulose membrane. A cellulose absorbent pad (4 mm×10 mm) was placed just upstream of the nitrocellulose assay membrane to serve as a rinse buffer reservoir.

Magnetic Enrichment Lateral Flow Immunoassay Protocol. A recombinant pan-malarial aldolase antigen (product #AGPV-55) and a recombinant PfHRP2 antigen (product #AGPF-55) were purchased from Immunology Consultants Laboratory (Newberg, Oreg.). A second source of PfHRP2 antigen was a sample of human plasma from a malaria patient, obtained onsite in Kisumu, Kenya through a collaboration between PATH (Seattle, Wash.) and the Walter Reed Army Institute of Research (WRAIR). Blood samples from 5-10 year old children presenting to outpatient clinics with fever were processed to yield plasma samples. Blood smear histology was used to estimate the parasitemia level, which was found to be 451,000 parasites/μL for the sample used in this report. The sample was also confirmed positive for 16s rRNA of *Plasmodium Falciparum* (sequences proprietary) using real time quantitative PCR performed by Epoch Biosciences. The clinical sample was also tested and found positive for PfHRP2 protein by ELISA. Pooled human rediscovered plasma in disodium EDTA (Valley Biomedical Inc., product #HP1051) was centrifuged at 1000×g for 30 minutes, and filtered through GDX graded syringe filters (Whatman) prior to use. The recombinant antigen(s) were spiked into 250 μL of pooled plasma. For the clinical antigen source, 1 μL of PfHRP2-positive plasma was diluted into 250 μL of pooled human plasma. One nM of the biotinylated anti-PfHRP2 IgG antibodies was then added to the pooled human plasma, followed by 2×PBS at pH 8.3. Next, SA-AuNPs (2 nM) were added, followed by homo-pNIPAAm mNPs (1 mg/mL), and 8 kDa homo-pNIPAAm free polymer (2 mg/mL). The total volume of the sample after addition of all reagents was 500 μL (i.e., 50% plasma (v/v)). For multiplexed detection of PfHRP2 and aldolase, 1 nM of anti-aldolase IgG was also included in the reaction mixture.

Phase transitioning of the thermally-responsive nanoparticle mixtures was achieved by heating the mixture for 15 minutes to 40° C. with orbital shaking in an aluminum tube holder equilibrated in an incubator. The sample was then incubated at 40° C. for an additional 15 minutes in close contact with a rare earth magnet (NdFeB, 1.27 cm×0.63 cm, Br max=12.1 kGauss). Next, the supernatant was carefully removed and discarded, and the AuNP/mNP aggregates captured along the wall of the Eppendorf tube were redissolved in 10 μL of 1×PBS buffer (pH 6.3, 4° C.), resulting in 50-fold volumetric enrichment. The enriched particle mixture was then applied onto the cellulose fibrous pad sitting on top of the modified lateral flow assay device. The liquid was allowed to wick into the strip for 60 seconds, after which 60 μL of the rinse buffer included in the commercial kit was applied to the strips to chase the AuNP/mNP mixture. The test was allowed to develop for 6-7 minutes in total, followed by removal of the absorbent pads, air drying, and imaging.

Image Acquisition and Analysis. Lateral flow membranes were mounted onto glass slides and imaged using a flatbed scanner (ScanMaker i900, MicroTek International, Inc.) at 900 dpi in 48-bit RGB mode. Images of the flow strips were analyzed using the NIH Image J software package. The integrated green channel pixel intensity at the anti-PfHRP2 test line of the lateral flow membranes was measured as a function of recombinant biomarker concentration to generate the standard curve. All samples were run in triplicate and plotted as mean±SD.

Magnetic Enrichment Lateral Flow Immunoassay. The magnetic enrichment lateral flow immunoassay proceeded in two stages, the first of which was the sample purification/enrichment stage, followed by the second lateral flow immunochromatography stage. Sample purification/enrichment was achieved by adding biotinylated antibodies to the 50% human plasma sample containing spiked PfHRP2 antigen molecules at known concentration. After binding to the target biomarker (PfHRP2), the biotinylated antibodies were complexed with the SA-AuNP reagent. PNIPAAm-mNPs and homo-pNIPAAm free polymer were then added, followed by application of the thermal stimulus causing polymer phase transition and nanoparticle co-aggregation.

The small (about 10 nm) mNPs used here undergo a thermally triggered magnetophoresis behavior. Below the LCST the non-aggregated mNPs were not separable in a modest magnetic field of an NdFeB magnet. Only when the thermally-responsive polymer corona was in the collapsed state were the mNPs able to form large aggregates that were rapidly magnetophoresed and separated from solution. Formation of large aggregates with a significant degree of co-mingling of AuNPs and mNPs was therefore necessary to achieve high-efficiency AuNP magnetic separation via the co-aggregation mechanism. The aggregates used to achieve high-efficiency separation of the AuNPs were very large (>μm) and underwent visible sedimentation.

Experiments were first performed to optimize the AuNP capture efficiency. The solution absorbance at 530 nm was measured before and after magnetic separation and resuspension of the captured aggregates into an equal volume of cool (4° C.) buffer. Higher separation efficiency was achieved by first applying the thermal stimulus in the absence of a magnetic field for 15 minutes on an orbital shaker. This allowed sufficient interaction time for the particles to form large aggregates of sufficient size to be magnetically separated. After this initial aggregation time, the mixed AuNP/mNP sample solution was turbid with visible precipitate. The co-aggregated particle mixture was then placed in close proximity to the magnet for 15 minutes resulting in magnetophoresis of the gold particles bound to the target biomarkers. Typical particle capture efficiency after 15 minutes of heating with orbital shaking, followed by 15 minutes of magnetic separation in 50% human plasma was about 85%.

After magnetic separation of about 85% of the gold nanoparticles, the second immunochromatography stage of the assay proceeded by careful removal of the supernatant with a pipette. 10 μL of cold PBS buffer at pH 6.3 was then applied directly to the captured aggregates as the magnetic field was removed. The slightly acidic pH of the resuspension buffer was chosen to protonate amine groups on the polymer to aid in the disaggregation of the AuNPs. 7 μL of the enriched particle mixture was then applied directly to the cellulose fiber pad sitting atop the nitrocellulose assay membrane. The purpose of the cellulose fiber pad was to contain the liquid sample during the imbibition process, and prevent the liquid droplet from spreading on the flow strip. After 60 seconds, imbibition of the fluid by the flow strip was complete, and the rinse buffer was applied to chase the enriched sample solution. The strip was allowed to develop for 6-7 minutes, followed by imaging on a flat bed scanner in 48-bit RGB.

The performance of the immunoassay with magnetic enrichment described above was evaluated for comparison purposes against the unmodified commercial lateral flow immunoassay using the same solid phase functionalized membrane. For the commercial assay, an equal volume (7 μL, 50% human plasma) of sample containing the target PfHRP2 biomarker at known concentration was applied to the dry gold conjugate pad through the sample application port of the lateral flow device cassette. After 60 seconds, the included rinse buffer was applied to the buffer port, and the test was allowed to develop for 6-7 minutes. Imaging and analysis were performed identically as for the magnetic enrichment immunoassay.

FIG. 17A shows scanned images obtained after performing a 50-fold enrichment assay (top row), or a conventional non-enriched assay (bottom row) with the commercial gold conjugate in the flow strip cassette. Visual inspection of the flow strips showed that the assay performed with enrichment resulted in darker and thicker bands of gold colloid absorbance as compared with the assay performed without enrichment for a given sample volume applied to the flow strip. FIG. 17B is a plot of the green channel pixel intensity vs. distance along the flow strip for the samples that were enriched 50-fold.

The signal at the test line for both the enriched and non-enriched sample flow strips was integrated and plotted (mean±SD, n=3) as a function of the target biomarker concentration, as shown in FIG. 17C. The signal response was significantly steeper for the assay with 50-fold magnetic enrichment. The background noise of the assay at zero antigen was not increased by magnetic enrichment. A recombinant PfHRP2 concentration of 10 ng/mL was clearly visualized by the magnetic enrichment assay, but was not detectable with the conventional flow strip. At 25 ng/mL, the commercial assay was only barely visible while the assay with 50-fold enrichment shows very strong signal. These results show how enrichment can improve the signal to noise of lateral flow biosensors. Although the system did not incorporate optimized surfactants/buffer mixtures or matched antibodies, it was still competitive with the current flow strips or better than them on a per volume basis.

Effect of Increasing Sample Volume on Signal Generation from a Clinical Sample. To demonstrate how volumetric enrichment can increase the signal for a given sample composition with clinical relevance, samples of 50% pooled human plasma spiked with PfHRP2 biomarkers derived from an in vivo human PfHRP2 infection were tested. Samples of human plasma were collected on site in Kisumu, Kenya by a collaborator (PATH, Seattle, Wash.), and shipped to Seattle, Wash. The clinical plasma sample was tested by RT-qPCR and confirmed positive for *Plasmodium Falciparum* infection. Microscopy analysis showed that the parasitemia level was approximately 450,000 parasites/μL. The sample was also tested for PfHRP2 antigen by ELISA and found to be a strong positive. The clinical plasma sample was then diluted into pooled human plasma (1:250) for the volumetric enrichment studies.

The 1:250 dilution of the clinical PfHRP2 antigen was sequentially complexed with the biotinylated anti-PfHRP2 IgG antibody, the SA-AuNPs, and eventually the mNPs via the "smart" polymer. Samples were split into 100 or 500 μL aliquots that were magnetically processed in parallel. After separation, the aggregates were re-suspended into 10 μL of cold PBS buffer (pH 6.3), representing a 10-fold or 50-fold volumetric enrichment factor for the 100 and 500 μL sample aliquots, respectively. 7 μL of the enriched particle mixture was then applied to the flow strips and developed.

As shown in FIG. 18A (top), the signal generated from the diluted PfHRP2 clinical sample was measured while varying the total processed volume from 100 to 500 μL. The true positive result (two stripes of colloidal absorbance, test and control lines) was only obtained for a processed sample volume of 500 µL. When a 100 µL volume was processed and flowed through the strip, no detectable signal at the test line was observed because the target biomarker in the 10-fold enriched sample was too dilute. The intensity at the control line was significantly higher for the enriched sample due to an increased concentration of AuNPs.

The 50-fold enriched samples also exhibited increased viscosity as compared with the 10-fold enriched samples, which tended to slow down the flow through the nitrocellulose assay membrane giving the AuNPs a longer interaction time with the capture antibodies immobilized at the test and control lines. An increase in residence time due to viscosity differences in addition to volumetric concentration effects contributed to larger signal for the enriched sample. These observations demonstrate how volumetric enrichment by the "smart" nanoparticle mixtures boosts the signal for a highly relevant clinical biomarker.

The effects of volumetric enrichment on the assay noise was assessed, as shown in FIG. 18A (bottom). The pooled human plasma that was used as the diluent for the clinical antigen was tested without addition of the clinical PfHRP2 antigen molecules. The assay noise remained low at both 100 and 500 µL processed volume of 50% plasma. That there is no difference in the background noise regardless of the volume processed speaks to the high specificity of the antibodies used.

Shown in FIG. 18B are line scans of the mean green channel pixel intensity plotted vs. distance along the strip. The line scan at a 500 µL processed volume shows the darkened pixel intensity at both lines (test and control), while at a 100 µL processed volume only signal from the control line is seen. FIG. 18C shows the integrated green channel pixel intensity (mean±SD, n=3) at the test line for the clinical PfHRP2 positive sample ("signal") and for the pooled plasma sample with no PfHRP2 ("noise"). All pixel intensity scales are plotted on an inverted axis for clarity.

Demonstration of Multiplexed Biomarker Enrichment and Lateral Flow Detection. Taking advantage of the universality of the SA-AuNP labeling reagent, the ability of mixtures of biotinylated antibodies to bind their respective antigen partners in a homogeneous sample mixture and then complex with the gold reagent was demonstrated. This allowed multiplexed detection of biomarkers without modifying any of the nanoparticle reagents. For multiplexed detection, the recombinant PfHRP2 and pan-malarial aldolase antigens were spiked into pooled human plasma. Two different biotinylated antibodies, each specific for one of the two antigens, were then added (1 nM each) to the sample to bind their respective antigens. Next, PBS buffer containing the SA-AuNPs (3 nM), mNPs (1 mg/mL), and homo-pNIPAAm free polymer (2 mg/mL) were added, and the mixture was processed using the same heating, shaking, and magneto-enrichment protocol described above. The enriched particle mixture was flowed down the strip, sequentially through three capture lines. The line order (upstream to downstream) was anti-aldolase, followed by anti-PfHRP2, and lastly anti-mouse IgG control line. As shown in FIG. 19, the assay enabled differentiation between plasma samples that had been spiked with neither, one, or both of the target biomarker species.

It was found that the analytical sensitivity for the aldolase antigen was lower than that of the PfHRP2 antigen. In FIG. 19, the units for aldolase concentration are in µg/mL, while for PfHRP2 are in ng/mL. The lower sensitivity, may be due to a lower antibody affinity, or decreased antigen stability for the aldolase biomarker. These results demonstrate how the mixed AuNP/mNP particle system can be easily multiplexed without modification of any of the nanoparticle reagents. The advantages of multiplexed biomarker detection strategies have been demonstrated for a range of clinical diseases. A multiplexed approach is commonly used in diagnosing malaria infection to differentiate the multiple malaria species based on their specific PfHRP2 and pan-malarial aldolase biomarker expression profiles.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for concentrating a non-magnetic particle in a liquid, comprising:
    (a) applying a magnetic field to a mixture comprising a co-aggregate in a liquid to provide a collected co-aggregate in the liquid, wherein the co-aggregate comprises:
        (i) a magnetic particle having a stimuli-responsive polymer attached thereto; and
        (ii) a non-magnetic particle having a stimuli-responsive polymer attached thereto;
        wherein the non-magnetic particle further comprises a first binding partner of a binding pair, wherein the liquid comprises a second binding partner of the binding pair, and wherein the co-aggregate comprises a non-magnetic particle having the first and second binding partners attached thereto;
    (b) removing at least a portion of the liquid from the collected co-aggregate in the liquid;
    (c) re-dissolving the co-aggregate to provide a mixture comprising the magnetic particle having the stimuli-responsive polymer attached thereto and the non-magnetic particle having the stimuli-responsive polymer and first and second binding partners attached thereto; and
    (d) contacting the mixture comprising the magnetic particle having the stimuli-responsive polymer attached thereto and the non-magnetic particle having the stimuli-responsive polymer and first and second binding partners attached thereto with a solid phase effective to immobilize the non-magnetic particle having the stimuli-responsive polymer and first and second binding partners attached thereto.

2. The method of claim 1, wherein the co-aggregate further comprises free stimuli-responsive polymer.

3. A method for capturing a diagnostic target in a liquid medium, comprising:
    (a) contacting a liquid medium to be tested for the presence of a diagnostic target with a plurality of stimuli-responsive particles, wherein the plurality of stimuli-responsive particles comprises
        (i) a plurality of magnetic particles, each having a stimuli-responsive polymer attached thereto, and
        (ii) a plurality of non-magnetic particles, each having a stimuli-responsive polymer and a capture moiety attached thereto, wherein the capture moiety has an affinity to the diagnostic target,
        wherein the plurality of stimuli-responsive particles is contacted with the liquid medium for a pre-determined period of time sufficient to effect binding of the diagnostic target, if present, to a portion of the plurality of the non-magnetic particles; and
        wherein the liquid medium to be tested comprises a first and a second diagnostic target and the plurality of non-magnetic particles comprises
        (i) a plurality of first non-magnetic particles, each having a stimuli-responsive polymer and a first capture moiety attached thereto, wherein the first capture moiety has an affinity to the first diagnostic target, and (ii) a plurality of second non-magnetic particles, each having a stimuli-responsive polymer and a second capture moiety attached thereto, wherein the second capture moiety has an affinity to the second diagnostic target;

(b) applying an external stimulus to provide a co-aggregate in the liquid medium, wherein the co-aggregate comprises
  (i) a plurality of magnetic particles, each having a stimuli-responsive polymer attached thereto, and
  (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
  wherein the co-aggregate is formed by the association of the stimuli-responsive polymer attached to the magnetic particle to the stimuli-responsive polymer attached to the non-magnetic particle;

(c) subjecting the co-aggregate to a magnetic field to magnetophorese the co-aggregate to a site within the liquid medium to provide a magnetophoresced co-aggregate in the liquid medium;

(d) removing at least portion of the liquid medium from the liquid medium comprising the magnetophoresced co-aggregate to provide the co-aggregate and optionally residual liquid medium;

(e) removing the stimulus and the magnetic field to provide a mixture comprising
  (i) a plurality of magnetic particles, each having a stimuli-responsive polymer attached thereto,
  (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
  (iii) optionally residual liquid medium; and (f) contacting the mixture with a solid phase to immobilize at least a portion of the first plurality of non-magnetic particles having the first diagnostic target attached thereto and to immobilize at least a portion of the second plurality of non-magnetic particles having the second diagnostic target attached thereto.

4. The method of claim 3 further comprising contacting the mixture with a solid phase to immobilize at least a portion of the plurality of non-magnetic particles having the diagnostic target attached thereto.

5. The method of claim 3, wherein the diagnostic target is an antigen and the capture moiety is an antibody.

6. The method of claim 3, wherein the diagnostic target is a biomarker for a disease or disorder.

7. The method of claim 3, wherein the non-magnetic particles having the first diagnostic target attached thereto are immobilized on the solid phase at a first position and the non-magnetic particles having the second diagnostic target attached thereto are immobilized on the solid phase at a second position, wherein the first and second positions are not the same.

8. A method for capturing a diagnostic target in a liquid medium, comprising:

(a) contacting a liquid medium to be tested for the presence of a diagnostic target with a first binding partner having an affinity to the diagnostic target and plurality of stimuli-responsive particles, wherein the plurality of stimuli-responsive particles comprises (i) a plurality of magnetic particles, each having a stimuli-responsive polymer attached thereto, and (ii) a plurality of non-magnetic particles, each having a stimuli-responsive polymer and a second binding partner attached thereto, wherein the second binding partner has an affinity to the first binding partner, wherein the plurality of stimuli-responsive particles is contacted with the liquid medium for a pre-determined period of time sufficient to effect binding of the diagnostic target, if present, to a portion of the plurality of non-magnetic particles through the association of the first and second binding partners;

(b) applying an external stimulus to provide a co-aggregate in the liquid medium, wherein the co-aggregate comprises
  (i) a plurality of magnetic particles, each having a stimuli-responsive polymer attached thereto, and
  (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
  wherein the co-aggregate is formed by the association of the stimuli-responsive polymer attached to the magnetic particle to the stimuli-responsive polymer attached to the non-magnetic particle;

(c) subjecting the co-aggregate to a magnetic field to magnetophorese the co-aggregate to a site within the liquid medium to provide a magnetophoresced co-aggregate in the liquid medium;

(d) removing at least portion of the liquid medium from the liquid medium comprising the magnetophoresced co-aggregate to provide the co-aggregate and optionally residual liquid medium;

(e) removing the stimulus and the magnetic field to provide a mixture comprising
  (i) a plurality of magnetic particles, each having a stimuli-responsive polymer attached thereto,
  (ii) a plurality of non-magnetic particles, each having a stimuli-responsive polymer thereto, wherein at least a portion of the plurality of non-magnetic particles have the diagnostic target attached thereto when the diagnostic target is present in the liquid medium, and
  (iii) optionally residual liquid medium; and (f) contacting the mixture with a solid phase to immobilize at least a portion of the plurality of non-magnetic particles have the diagnostic target attached thereto.

9. The method of claim 8, wherein the liquid medium to be tested for a diagnostic target is to be tested for first and second diagnostic targets, wherein contacting the liquid medium comprises contacting with a first binding partner having an affinity to the first diagnostic target, a third binding partner having an affinity to the second diagnostic target, and plurality of stimuli-responsive particles, wherein the plurality of stimuli-responsive particles comprises (i) a plurality of magnetic particles, each having a stimuli-responsive polymer attached thereto, (ii) a plurality of first non-magnetic particles, each having a stimuli-responsive polymer and a second binding partner attached thereto, wherein the second binding partner has an affinity to the first binding partner, and (iii) a plurality of second non-magnetic particles, each having a stimuli-responsive polymer and a fourth binding partner attached thereto, wherein the fourth binding partner has an affinity to the third binding partner, wherein the plurality of stimuli-responsive particles is contacted with the liquid medium for a pre-determined period of time sufficient to effect binding of the first and second diagnostic targets, if present, to a portion of the pluralities of the first and second non-magnetic particles through the association of the first and second, and third and fourth binding partners, respectively.

10. The method of claim 9 further comprising contacting the mixture with a solid phase to immobilize at least a portion of the plurality of first non-magnetic particles having the first diagnostic target attached thereto and to immobilize at least a portion of the plurality of second non-magnetic particles having the second diagnostic target attached thereto.

11. The method of claim 10, wherein the non-magnetic particles having the first diagnostic target attached thereto are immobilized on the solid phase at a first position and the non-magnetic particles having the second diagnostic target attached thereto are immobilized on the solid phase at a second position, wherein the first and second positions are not the same.

* * * * *